United States Patent
Ost

(10) Patent No.: US 10,563,248 B2
(45) Date of Patent: Feb. 18, 2020

(54) OXIDIZING AGENT FOR MODIFIED NUCLEOTIDES

(71) Applicant: Cambridge Epigenetix Limited, Cambridge (GB)

(72) Inventor: Toby Ost, Babraham (GB)

(73) Assignee: Cambridge Epigenetix Limited, Cambourne (GB)

( * ) Notice: Subject to any disclaimer, the term of this patent is extended or adjusted under 35 U.S.C. 154(b) by 521 days.

(21) Appl. No.: 14/648,527

(22) PCT Filed: Nov. 28, 2013

(86) PCT No.: PCT/EP2013/074995
§ 371 (c)(1),
(2) Date: May 29, 2015

(87) PCT Pub. No.: WO2014/083118
PCT Pub. Date: Jun. 5, 2014

(65) Prior Publication Data
US 2015/0299781 A1 Oct. 22, 2015

Related U.S. Application Data

(60) Provisional application No. 61/761,521, filed on Feb. 6, 2013, provisional application No. 61/731,941, filed on Nov. 30, 2012.

(51) Int. Cl.
*C12Q 1/6827* (2018.01)
(52) U.S. Cl.
CPC ..... *C12Q 1/6827* (2013.01); *C12Q 2600/154* (2013.01)
(58) Field of Classification Search
None
See application file for complete search history.

(56) References Cited

U.S. PATENT DOCUMENTS

| | | |
|---|---|---|
| 8,257,950 B2 | 9/2012 | Berlin et al. |
| 8,653,007 B2 | 2/2014 | Zheng et al. |
| 8,679,745 B2 | 3/2014 | Ballhause et al. |
| 8,741,567 B2 | 6/2014 | He et al. |
| 8,822,146 B2 | 9/2014 | Klimasauskas et al. |

(Continued)

FOREIGN PATENT DOCUMENTS

| | | |
|---|---|---|
| CN | 105648537 A | 6/2016 |
| EP | 0377521 A1 | 7/1990 |

(Continued)

OTHER PUBLICATIONS

Nestor et al. BioTechniques. 2010. 48:317-319. (Year: 2010).*

(Continued)

*Primary Examiner* — Joseph G. Dauner
(74) *Attorney, Agent, or Firm* — Wilson Sonsini Goodrich & Rosati

(57) ABSTRACT

This invention relates to the use of metal (VI) oxo complexes to catalyse the selective oxidation of 5hmC residues in polynucleotides to 5fC residues. This may be useful in the identification of modified cytosine residues in a population of polynucleotides comprising a sample nucleotide sequence. A first portion of the population is oxidised with a metal (VI) oxo complex and then the first portion and a second portion of said population are both treated with bisulfite. The residues in the first and second portions that correspond to a cytosine residue in the sample nucleotide sequence are identified following treatment and the identities of these residues are used to determine the modification of the cytosine residue in the sample nucleotide sequence. Methods, reagents and kits are provided.

16 Claims, 6 Drawing Sheets

Specification includes a Sequence Listing.

| Base | Sequence | BS Sequence | oxBS Sequence |
|---|---|---|---|
| C | C | T | T |
| 5mC | C | C | C |
| 5hmC | C | C | T |

(56) References Cited

U.S. PATENT DOCUMENTS

| | | |
|---|---|---|
| 8,889,352 B2 | 11/2014 | Klimasauskas et al. |
| 8,895,244 B2 | 11/2014 | Okamoto et al. |
| 8,951,736 B2 | 2/2015 | Schmidt |
| 8,962,246 B2 | 2/2015 | Ballhause et al. |
| 8,969,061 B2 | 3/2015 | Zhu et al. |
| 9,029,087 B2 | 5/2015 | Zheng et al. |
| 9,034,597 B2 | 5/2015 | Bitinaite et al. |
| 9,040,239 B2 | 5/2015 | Zheng et al. |
| 9,115,386 B2 | 8/2015 | Rao et al. |
| 9,121,061 B2 | 9/2015 | Vaisvila et al. |
| 9,145,580 B2 | 9/2015 | Feehery et al. |
| 9,150,918 B2 | 10/2015 | Turner et al. |
| 9,175,338 B2 | 11/2015 | Flusberg et al. |
| 9,175,341 B2 | 11/2015 | Flusberg et al. |
| 9,175,348 B2 | 11/2015 | Korlach et al. |
| 9,200,260 B2 | 12/2015 | Correa, Jr. et al. |
| 9,200,316 B2 | 12/2015 | Zheng et al. |
| 9,238,836 B2 | 1/2016 | Korlach et al. |
| 9,243,233 B2 | 1/2016 | Rim et al. |
| 9,267,117 B2 | 2/2016 | Guan et al. |
| 9,290,807 B2 | 3/2016 | Booth et al. |
| 9,297,806 B2 | 3/2016 | Yegnasubramanian et al. |
| 9,347,093 B2 | 5/2016 | Klimasauskas et al. |
| 9,447,452 B2 | 9/2016 | Rao et al. |
| 9,464,277 B2 | 10/2016 | Zheng et al. |
| 9,505,797 B2 | 11/2016 | Klimasauskas et al. |
| 9,546,400 B2 | 1/2017 | Turner et al. |
| 9,567,633 B2 | 2/2017 | Gao et al. |
| 9,611,510 B2 | 4/2017 | He et al. |
| 9,650,675 B2 | 5/2017 | Rimseliene et al. |
| 9,677,128 B2 | 6/2017 | Robertson et al. |
| 9,816,986 B2 | 11/2017 | Rao et al. |
| 9,822,394 B2 | 11/2017 | Ost et al. |
| 9,879,315 B2 | 1/2018 | Summerer et al. |
| 9,915,655 B2 | 3/2018 | Bensimon et al. |
| 9,988,673 B2 | 6/2018 | Klimasauskas et al. |
| 1,003,113 A1 | 7/2018 | Rao et al. |
| 1,008,182 A1 | 9/2018 | Guan et al. |
| 1,015,593 A1 | 12/2018 | Vaisvila et al. |
| 2004/0048279 A1 | 3/2004 | Olek et al. |
| 2004/0132026 A1 | 7/2004 | Olek |
| 2007/0026393 A1 | 2/2007 | Berlin et al. |
| 2007/0037184 A1 | 2/2007 | Boyd et al. |
| 2007/0269824 A1 | 11/2007 | Albrecht et al. |
| 2010/0167942 A1 | 7/2010 | Zheng et al. |
| 2010/0197510 A1 | 8/2010 | Spain et al. |
| 2011/0059432 A1 | 3/2011 | Ballhause et al. |
| 2012/0064521 A1 | 3/2012 | Yen et al. |
| 2013/0230856 A1 | 9/2013 | Schneider et al. |
| 2014/0030727 A1 | 1/2014 | Pfeifer et al. |
| 2014/0045183 A1* | 2/2014 | Okamoto ............ C12Q 1/6827 435/6.11 |
| 2014/0178873 A1 | 6/2014 | Brachmann et al. |
| 2014/0179564 A1 | 6/2014 | Korlach et al. |
| 2014/0228231 A1 | 8/2014 | Vilain et al. |
| 2014/0272970 A1 | 9/2014 | Zegzouti et al. |
| 2014/0363815 A1 | 12/2014 | Dahl et al. |
| 2015/0004596 A1 | 1/2015 | Zhu et al. |
| 2015/0011403 A1 | 1/2015 | Lo et al. |
| 2015/0056616 A1 | 2/2015 | He et al. |
| 2015/0240310 A1 | 8/2015 | Bitinaite et al. |
| 2015/0285807 A1 | 10/2015 | Shi et al. |
| 2015/0307542 A1 | 10/2015 | Roy et al. |
| 2016/0046981 A1 | 2/2016 | Correa, Jr. et al. |
| 2016/0115525 A1 | 4/2016 | Ebenstein et al. |
| 2016/0186207 A1 | 6/2016 | Reik et al. |
| 2016/0194696 A1 | 7/2016 | Guan et al. |
| 2016/0222448 A1 | 8/2016 | Horvath |
| 2016/0251700 A1 | 9/2016 | Ost et al. |
| 2016/0258014 A1 | 9/2016 | Booth et al. |
| 2016/0304552 A1 | 10/2016 | Roy et al. |
| 2017/0051354 A1 | 2/2017 | Davis et al. |
| 2017/0067093 A1 | 3/2017 | Klimasauskas et al. |
| 2017/0145484 A1 | 5/2017 | Rao et al. |
| 2017/0168043 A1 | 6/2017 | Rao et al. |
| 2017/0175085 A1 | 6/2017 | Rao et al. |
| 2017/0175129 A1 | 6/2017 | Roy et al. |
| 2017/0176420 A1 | 6/2017 | Rao et al. |
| 2017/0176421 A1 | 6/2017 | Rao et al. |
| 2017/0191119 A1 | 7/2017 | Rao et al. |
| 2017/0198344 A1 | 7/2017 | Vaisvila et al. |
| 2017/0218338 A1 | 8/2017 | Rao et al. |
| 2017/0219589 A1 | 8/2017 | Rao et al. |
| 2017/0253924 A1 | 9/2017 | Lu et al. |
| 2017/0283863 A1 | 10/2017 | Robertson et al. |
| 2017/0298422 A1 | 10/2017 | Song et al. |
| 2018/0044632 A1 | 2/2018 | Rao et al. |
| 2018/0044633 A1 | 2/2018 | Rao et al. |
| 2018/0105884 A1 | 4/2018 | Lo et al. |
| 2018/0112206 A1 | 4/2018 | Forsyth |
| 2018/0119113 A1 | 5/2018 | Rao et al. |
| 2018/0119225 A1 | 5/2018 | Rao et al. |
| 2018/0171397 A1 | 6/2018 | Vaisvila et al. |
| 2018/0201993 A1 | 7/2018 | Turner et al. |
| 2018/0223332 A1 | 8/2018 | Ost |
| 2018/0245128 A1 | 8/2018 | He et al. |
| 2018/0251815 A1 | 9/2018 | Okamoto et al. |
| 2018/0258149 A1 | 9/2018 | Motz et al. |
| 2018/0258474 A1 | 9/2018 | Jain et al. |
| 2018/0312914 A1 | 11/2018 | Vaisvila et al. |
| 2018/0327855 A1 | 11/2018 | Ebenstein et al. |
| 2019/0017109 A1 | 1/2019 | Song et al. |

FOREIGN PATENT DOCUMENTS

| | | |
|---|---|---|
| EP | 0652321 A1 | 5/1995 |
| EP | 1320632 B1 | 6/2006 |
| EP | 1394173 B9 | 10/2008 |
| EP | 2376632 A1 | 10/2011 |
| EP | 2414527 A1 | 2/2012 |
| EP | 2414528 A1 | 2/2012 |
| EP | 2470675 A1 | 7/2012 |
| EP | 2292797 B1 | 7/2013 |
| EP | 2630257 A1 | 8/2013 |
| EP | 2694686 A2 | 2/2014 |
| EP | 2776575 A1 | 9/2014 |
| EP | 2791361 A1 | 10/2014 |
| EP | 2825645 A2 | 1/2015 |
| EP | 2948774 A1 | 12/2015 |
| EP | 3013979 A1 | 5/2016 |
| EP | 3053585 A1 | 8/2016 |
| EP | 3061764 A1 | 8/2016 |
| EP | 3124605 A1 | 2/2017 |
| EP | 3214183 A1 | 9/2017 |
| WO | WO-9218134 A1 | 10/1992 |
| WO | WO-2009049916 A2 | 4/2009 |
| WO | WO-2010037001 A2 | 4/2010 |
| WO | 2012138973 | 10/2012 |
| WO | WO-2012141324 A1 | 10/2012 |
| WO | WO-2013017853 A2 | 2/2013 |
| WO | WO-2014083118 A1 | 6/2014 |
| WO | WO-2015043493 A1 | 4/2015 |
| WO | WO-2015048665 A2 | 4/2015 |
| WO | WO-2015124955 A1 | 8/2015 |
| WO | WO-2015145133 A1 | 10/2015 |
| WO | WO-2016016639 A1 | 2/2016 |
| WO | WO-2016034908 A1 | 3/2016 |
| WO | WO-2016063034 A1 | 4/2016 |
| WO | WO-2016063059 A1 | 4/2016 |
| WO | WO-2016079509 A1 | 5/2016 |
| WO | WO-2016170319 A1 | 10/2016 |
| WO | WO-2016189288 A1 | 12/2016 |
| WO | WO-2017039002 A1 | 3/2017 |
| WO | WO-2018129120 A1 | 7/2018 |
| WO | WO-2018165459 A1 | 9/2018 |

OTHER PUBLICATIONS

Marjerrison et al. Inorg Chem. 2016. 55:12897-12903. (Year: 2016).*

Booth et al., "Quantitative sequencing of 5-methylcytosine and 5-hydroxymethylcytosine at single-base resolution", Science, 2012, 336:934-937.

(56) References Cited

OTHER PUBLICATIONS

Flusberg et al., "Direct detection of DNA methylation during single-molecule, real-time sequencing", Nature Methods, 2010, 7:461-465.
Szwagierczak et al., "Sensitive enzymatic quantification of 5-hydroxymethylcytosine in genomic DNA", Nucleic Acids Research, 2010, 38:e181.1-E181.5.
Jin et al., "Examination of the specificity of DNA methylation profiling techniques towards 5-methylcytosine and 5-hydroxymethylcytosine", Nucleic Acids Res, 2010, 38:e125.
Fraga et al., "DNA methylation: a profile of methods and applications", Biotechniques, 2002, 33:632, 634, 636-49.
Oakeley et al., "DNA methylation analysis: a review of current methodologies", Pharmacol Ther, 1999, 84:389-400.
Office action dated Jul. 25, 2017 for U.S. Appl. No. 15/440,319.
Office action dated Aug. 8, 2017 for U.S. Appl. No. 15/440,284.
Deaton et al., "CpG islands and the regulation of transcription", Genes & Development, 2011, 25:1010-1022.
Tahiliani et al., "Conversion of 5-Methylcytosine to 5-Hydroxymethylcytosine in Mammalian DNA by MLL Partner TET1", Science, 2009; 324 930-935.
Ito et al., "Role of Tet proteins in 5mC to 5hmC conversion, ES cell self-renewal, and ICM specification", Nature, 2010, 466:1129-1133.
Koh et al., Tet1 and Tet2 regulate 5-hydroxymethylcytosine production and cell lineage specification in mouse embryonic stem cells, Cell Stem Cell, 2011, 8:200-213.
Ficz et al., "Dynamic regulation of 5-hydroxymethylcytosine in mouse ES cells and during differentiation", Nature, 2011, 473:398-401.
Williams et al., "Tet1 and hydroxymethylcytosine in transcription and DNA methylation fidelity", Nature, 2011, 473: 343-348.
Pastor et al., "Genome-wide mapping of 5-hydroxymethylcytosine in embryonic stem cells", Nature, 2011, 473: 394-397.
Xu et al., "Genome-wide Regulation of 5hmC, 5mC and Gene Expression by Tet1 Hydroxylase in Mouse Embryonic Stem Cells", Mol Cell., 2011, 42:451-464.
Branco et al., "Uncovering the role of 5-hydroxymethylcytosine in the epigenome", Nature Rev Genet, 2011, 7-13.
Kriaucionis et al., "The nuclear DNA base, 5-hydroxymethylcytosine is present in brain and enriched in Purkinje neurons", Science, 2009, 324:929-930.
Munzel et al., "Quantification of the Sixth DNA Base Hydroxymethylcytosine in the Brain", Angew. Chem. Int. Ed, 2010, 49:5375-5377.
Wu et al., "Genome-wide analysis of 5-hydroxymethylcytosine distribution reveals its dual function in transcriptional regulation in mouse embryonic stem cells", Genes & Development, 2011, 25:679-684.
Jin et al., "Genomic mapping of 5-hydroxymethylcytosine in the human brain", Nucleic Acids Research, 2011, 39:5015-5024.
Song et al., "Selective chemical labeling reveals the genome-wide distribution of 5-hydroxymethylcytosine", Nat Biotechnol, 2011, 29:68-72.
Frommer et al., "A genomic sequencing protocol that yields a positive display of 5-methylcytosine residues in individual DNA strands", Proc. Natl Acad. Sci., 1992, 89:1827-1831.
Huang et al., "The Behaviour of 5-Hydroxymethylcytosine in Bisulfite Sequencing", PLoS One, 2010, 5:e8888.
Nestor et al., "Enzymatic approaches and bisulfite sequencing cannot distinguish between 5-methylcytosine and 5-hydroxymethylcytosine in DNA", BioTechniques, 2010, 48:317-319.
Song et al., "Sensitive and specific single-molecule sequencing of 5-hydroxymethylcytosine", Nat Methods, 2013, 9: 75-77.
Eid et al., "Real-Time DNA Sequencing from Single Polymerase Molecules", Science, 2009, 323:133-138.
Wallace et al., "Identification of epigenetic DNA modifications with a protein nanopore", Chem Commun (Camb), 2010, 46:8195-8197.
Wanunu et al., "Discrimination of methylcytosine from hydroxymethylcytosine in DNA molecules", J Am Chem Soc, 2011, 133:486-492.
Wu et al., "Dnmt3a-Dependent Nonpromoter DNA Methylation Facilitates Transcription of Neurogenic Genes", Science, 2010, 329:444-448.
Van den Boom et al., "Mass Spectrometric Analysis of Cytosine Methylation by Base-Specific Cleavage and Primer Extension Methods", In DNA Methylation: Methods and Protocols, (Second Edition, 2009, J. Tost (ed)), 507:207-227.
Howell et al., "Dynamic allele-specific hybridization", Nature Biotechnology, 1999, 17:87-88.
Abravaya et al., "Molecular Beacons as Diagnostic Tools: Technology and Applications", Clin. Chem. Lab. Med, 2003, 41:468-74.
Newton et al., "Analysis of any point mutation in DNA. The amplification refractory mutation system (ARMS)", Nucl. Acids Res., 1989, 17:2503-2516.
Wu et al., "Allele-specific enzymatic amplification of fbeta-globin genomic DNA for diagnosis of sickle cell anemia", Proc Natl Acad Sci USA, 1989, 86:2757-2760.
Okayama et al., "Rapid, nonradioactive detection of mutations in the human genome by allele-specific amplification", J. Lab. Clin. Med., 1989, 114:105-113.
Olivier et al., "The Invader® assay for SNP genotyping", Mutat. Res., 2005, 573:103-10.
Gunderson et al., "Whole-Genome Genotyping", Meth. Enzymol. Methods in Enzymology, 2006, 410:359-76.
Syvanen et al., "Accessing genetic variation: Genotyping single nucleotide polymorphisms", Nat. Rev. Genet., 2001, 2:930-42.
McGuigan et al., "Single nucleotide polymorphism detection: allelic discrimination using TaqMan", Psychiatr. Genet. 2002, 12:133-6.
Jarvius et al., "Oligonucleotide Ligation Assay", In Methods in Molecular Biology, (Kwok (ed)), 2003, 212:215-228.
Sanger et al., "DNA sequencing with chain-terminating inhibitors", Proc Natl Acad Sci USA, 1977, 74:5463-5467.
Bentley et al., "Accurate Whole Human Genome Sequencing using Reversible Terminator Chemistry", Nature, 2008, 456:53-59.
McKernan et al., "Sequence and structural variation in a human genome uncovered by short-read, massively parallel ligation sequencing using two-base encoding", Genome Res, 2009, 19:1527-1541.
Ronaghi et al., "A Sequencing Method Based on Real-Time Pyrophosphate", Science, 1998, 281:363-365.
Korlach et al., "Real-Time DNA Sequencing from Single Polymerase Molecules", Methods in Enzymology, 2010, 472:431-455.
Rothberg et al., "An integrated semiconductor device enabling non-optical genome sequencing", Nature, 2011, 475:348-352.
Li et al., "Distribution of 5-Hydroxymethylcytosine in Different Human Tissues", J Nucleic Acids, 2011, 870726.
Pfaffeneder, T. et al., "The Discovery of 5-Formylcytosine in Embryonic Stem Cell DNA", Angew, 2011, 50:1-7008-7012.
Maeda et al., "A Simple and Rapid Method for HLA-DP Genotyping by Digestion of PCR-Amplified DNA with Allele-Specific Restriction Endonucleases", Hum Immunol, 1990, 27:111-21.
Wang et al., "Improved adapter-ligation-mediated allele-specific amplification for multiplex genotyping by using software", Electrophoresis, 2008, 29:1490-501.
Wolff et al., "Combining allele-specific fluorescent probes and restriction assay in real-time PCR to achieve SNP scoring beyond allele ratios of 1:1000", BioTechniques, 2008, 44:193-199.
Zhang et al., "SNP Cutter: a comprehensive tool for SNP PCR-RFLP assay design", Nucleic Acids Res, 2005, 33: W489-92.
Hung et al., "Comparison of the mismatch-specific endonuclease method and denaturing high-performance liquid chromatography for the identification of HBB gene mutations", BMC Biotechnology, 2008, 8:62.
Lister et al., "Highly Integrated Single-Base Resolution Maps of the Epigenome in *Arabidopsis*", Cell, 2008, 133: 523-536.
Wang et al., "Comparison of bisulfite modification of 5-methyldeoxycytidine and deoxycytidine residues", Nucleic Acids Research, 1980, 8:4777-4790.
Hayatsu et al., "Accelerated bisulfite-deamination of cytosine in the genomic sequencing procedure for DNA methylation analysis", Nucleic Acids Symposium Series, 2004, No. 48:261-262.

(56) References Cited

OTHER PUBLICATIONS

Lister et al., "Human DNA methylomes at base resolution show widespread epigenomic differences", Nature, 2009, 462:315-322.
Booth, M.J., et al. (2013). Oxidative Bisulfite Sequencing of 5-Methylcytosine and 5-Hydroxymethylcytosine. Nat. Protoc. 8, 1841-1851.
Borgel, et al. Targets and Dynamics of Promoter DNA Methylation During Early Mouse Development, Nature Genetics 42 (2010): 1093-1101.
Burdzy, et al. Synthesis of stable-isotope enriched 5-methylpyrimidines and their use as probes of base reactivity in DNA. Nucleic Acids Res. Sep. 15, 2002; 30(18): 4068-4074.
Clark, et al. Enhanced 5-methylcytosine detection in single-molecule, real-time sequencing via Tet1 oxidation. BMC Biol. Jan. 22, 2013;11:4. doi: 10.1186/1741-7007-11-4.
European search report with written opinion dated Feb. 9, 2017 for EP16193069.
Ficz, et al. Reprogramming by cell fusion: boosted by Tets. Mol Cell. Mar. 28, 2013;49(6):1017-8. doi: 10.1016/j.molcel.2013.03.014.
Final Office Action dated Jan. 5, 2014 for U.S. Appl. No. 13/120,861.
Final Office Action dated Aug. 25, 2014 for U.S. Appl. No. 13/795,739.
Fu, Y. et al. (2012). Nucleic Acid Modifications With Epigenetic Significance. Curr. Opin. Chem. Biol. 16, 516-524.
Goodier, et al. A Novel Active L1 Retrotransposon Subfamily in the Mouse. Genome Research. 11 (2001): 1677-1685.
Green, et al. Oxo Complexes of Ruthenium(VI) and (VII) as Organic Oxidants. Journal of the Chemical Society (1984): 681-686.
Gu, et al. Preparation of reduced representation bisulfite sequencing libraries for genome-scale DNA methylation profiling. Nat Protoc. Apr. 2011;6(4):468-81. doi: 10.1038/nprot.2010.190. Epub Mar. 18, 2011.
Gupta, et al. Advances in Genome-wide DNA Methylation Analysis. Biotechniques 49 (2010): iii-xi.
He, et al. Tet-mediated formation of 5-carboxylcytosine and its excision by TDG in mammalian DNA. Science. Sep. 2, 2011;333(6047):1303-7. doi: 10.1126/science.1210944. Epub Aug. 4, 2011.
Hu et al., Discrimination between 5-hydroxymethylcytosine and 5-methylcytosine in DNA by selective chemical abeling. Bioorganic & Medicinal Chemistry Letters 24 (2014): 294-297.
Illingworth, et al. Orphan CpG Islands Identify Numerous Conserved Promoters in the Mammalian Genome. PLoS Genetics 6 (2010): 1-15.
International Search Report dated Feb. 14, 2013 for PCT/GB2012/051819.
International search report with written opinion dated Mar. 28, 2014 for PCT/EP2013/074995.
Ito, et al. Tet proteins can convert 5-methylcytosine to 5-formylcytosine and 5-carboxylcytosine. Science. Sep. 2, 2011;333(6047):1300-3. doi: 10.1126/science.1210597. Epub Jul. 21, 2011.
Johnson, et al. 5-Hydroxymethylcytosine localizes to enhancer elements and is associated with survival in glioblastoma patients. Nat Commun. Nov. 25, 2016;7:13177. doi: 10.1038/ncomms13177.
Kawasaki, et al. A Novel method for the simultaneous identification of methylcytosine and hydroxymethylcytosine at a single base resolution. Nucleic Acids Res. Oct. 24, 2016. pii: gkw994. [Epub ahead of print].
Kinney, et al. Tissue-Specific Distribution and Dynamic Changes of 5-Hydroxymethylcytosine in Mammalian Genomes. The Journal of Biological Chemistry 286 (2011): 24685-24693.
Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.
Krueger, et al. Large scale loss of data in low-diversity illumina sequencing libraries can be recovered by deferred cluster calling. PLoS One. Jan. 28, 2011;6(1):e16607. doi: 10.1371/journal.pone.0016607.

Lane, et al. Resistance of IAPs to Methylation Reprogramming May Provide a Mechanism for Epigenetic Inheritance in the Mouse. Genesis 35 (2003): 88-93.
Meissner, et al. Genome-Scale DNA Methylation Maps of Pluripotent and Differentiated Cells. Nature 454 (2008): 766-770.
Mellen, M., et al. (2012). MeCP2 binds to 5hmC enriched within active genes and accessible chromatin in the nervous system. Cell 151, 1417-1430.
Nakano, et al. Oxidation of unsaturated and hydroxy fatty acids by ruthenium tetroxide and ruthenium oxyanions. Journal of the American Oil Chemists' Society Apr. 1982, vol. 59, Issue 4, pp. 163-166.
Nomura, et al. Discrimination Between 5-Hydroxymethylcytosine and 5-Methylcytosine by a Chemically Designed Peptide. Chemical Communications 47 (2011): 8277-8279.
Non-Final Office Action dated Oct. 3, 2016 for U.S. Appl. No. 15/054,227.
Non-Final Office Action dated Aug. 4, 2015 for U.S. Appl. No. 14/235,707.
Non-Final Office Action dated Sep. 8, 2014 for U.S. Appl. No. 13/120,861.
Non-Final Office Action dated Mar. 13, 2013 for U.S. Appl. No. 13/120,861.
Non-Final Office Action dated Sep. 16, 2013 for U.S. Appl. No. 13/120,861.
Non-Final Office Action dated Sep. 17, 2015 for U.S. Appl. No. 13/795,739.
Non-Final Office Action dated Mar. 24, 2014 for U.S. Appl. No. 13/795,739.
Notice of Allowance dated Nov. 12, 2015 for U.S. Appl. No. 14/235,707.
Office Action dated Jun. 13, 2017 for U.S. Appl. No. 15/440,822.
Office Action dated Jun. 28, 2017 for U.S. Appl. No. 15/440,826.
Office Action dated May 31, 2017 for U.S. Appl. No. 15/440,408.
Pacific Biosciences. Detecting DNA Base Modification Using Single Molecule, Real-Time Sequencing. Copyright 2012.
Qin, et al. Intracisternal A Particle Genes: Distribution in the Mouse Genome, Active Subtypes, and Potential Roles as Species-Specific Mediators of Susceptibility to Cancer. Molecular Carcinogenesis 49 (2010): 54-67.
Quinlivan, et al. DNA Digestion to Deoxyribonucleoside: A Simplified One-Step Procedure. Analytical Biochemistry 373 (2008): 383-385.
Raiber, et al. Genome-wide distribution of 5-formylcytosine in embryonic stem cells is associated with transcription and depends on thymine DNA glycosylase. Genome Biology 13.R69 (2012): 1-11.
Rodic, et al. Diagnostic utility of 5-hydroxymethylcytosine immunohistochemistry in melanocytic proliferations. J Cutan Pathol. Nov. 2015;42(11):807-14. doi: 10.1111/cup.12564. Epub Sep. 2, 2015.
Sachichman, et al. L1 A-Monomer Tandem Arrays Have Expanded During the Course of Mouse L1 Evolution. Molecular Biology and Evolution 10 (1993): 552-570.
Seisenberger, S., et al. (2012). The dynamics of genome-wide DNA methylation reprogramming in mouse primordial germ cells. Mol. Cell 48, 849-862.
Song, et al. Simultaneous single-molecule epigenetic imaging of DNA methylation and hydroxymethylation. Proc Natl Acad Sci U S A. Apr. 19, 2016;113(16):4338-43. doi: 10.1073/pnas.1600223113. Epub Mar. 28, 2016.
Stadler, et al. DNA-binding factors shape the mouse methylome at distal regulatory regions. Nature. Dec. 14, 2011;480(7378):490-5. doi: 10.1038/nature10716.
Tomaschewski, et al. T4-induced alpha- and beta-glucosyltransferase: cloning of the genes and a comparison of their products based on sequencing data. Nucleic Acids Res. Nov. 11, 1985; 13(21): 7551-7568.
Xia, et al. Bisulfite-free, base-resolution analysis of 5-formylcytosine at the genome scale. Nat Methods. Nov. 2015;12(11):1047-50. doi: 10.1038/nmeth.3569. Epub Sep. 7, 2015.
Yu, et al. Base-resolution analysis of 5-hydroxymethylcytosine in the mammalian genome. Cell. Jun. 8, 2012;149(6):1368-80. doi: 10.1016/j.cell.2012.04.027. Epub May 17, 2012.

(56) References Cited

OTHER PUBLICATIONS

Yu, et al. Tet-assisted bisulfite sequencing of 5-hydroxymethylcytosine. Nat Protoc. Dec. 2012;7(12):2159-70. doi: 10.1038/nprot.2012.137. Epub Nov. 29, 2012.

Lee, et al. Kinetics and mechanism of the oxidation of alcohols by ruthenate and perruthenate ions. Canadian journal of chemistry, 2011(2): 1773-779.

Matsushita; et al., "Matsushita, et al. DNA-friendly Cu(ii)/Tempo-catalyzed 5-hydroxymethylcytosine-specific oxidation. Chem Commun (Camb). May 23, 2017;53(42):5756-5759. doi: 10.1039/c7cc02814h.".

Office action dated Jan. 23, 2018 for U.S. Appl. No. 15/440,424.
Office action dated Apr. 16, 2018 for U.S. Appl. No. 15/341,344.
Office action dated Nov. 22, 2017 for U.S. Appl. No. 15/440,822.

Lenz, et al., Tetra-m-propylammonium perruthenate (TPAP)-catalysed oxidations of alcohols using molecular oxygen as a co-oxidant. J. Chem. Soc. Perkin Tran., 1997; 3291-3292.

Privat, et al., Photochemical Deamination and Demethylation of 5-Methylcytosine. Chem. Res. Toxicol., 1996;9 (4): pp. 745-750.

U.S. Appl. No. 15/193,796 Office Action dated Jun. 20, 2018.
U.S. Appl. No. 15/075,370 Office Action dated Sep. 21, 2018.
U.S. Appl. No. 15/440,815 Office Action dated Jun. 12, 2018.

\* cited by examiner

OXIDIZING AGENT FOR MODIFIED NUCLEOTIDES

CROSS REFERENCE TO RELATED APPLICATIONS

This application is the U.S. national stage of International (PCT) Patent Application No. PCT/EP2013/074995, filed Nov. 28, 2013, which claims the benefit of the priority dates of U.S. Provisional Application No. 61/731,941, filed Nov. 30, 2012, and U.S. Provisional Application No. 61/761,521, filed Feb. 6, 2013. The contents of these earlier-filed provisional applications are hereby incorporated by reference herein in their entirety.

This invention relates to reagents, and in particular oxidising agents, for use in the detection of modified cytosine residues and the analysis and/or sequencing of nucleic acids that contain modified cytosine residues.

5-methylcytosine (5mC) is a well-studied epigenetic DNA mark that plays important roles in gene silencing and genome stability, and is found enriched at CpG dinucleotides (1). In metazoa, 5mC can be oxidised to 5-hydroxymethylcytosine (5hmC) by the ten-eleven translocation (TET) family of enzymes (2, 3). The overall levels of 5hmC are roughly 10-fold lower than those of 5mC and vary between tissues (4). Relatively high quantities of 5hmC (~0.4% of all cytosines) are present in embryonic stem (ES) cells, where 5hmC has been suggested to have a role in the establishment and/or maintenance of pluripotency (2,3, 5-9). 5hmC has been proposed as an intermediate in active DNA demethylation, for example by deamination or via further oxidation of 5hmC to 5-formylcytosine (5fC) and 5-carboxycytosine (5cC) by the TET enzymes, followed by base excision repair involving thymine-DNA glycosylase (TDG) or failure to maintain the mark during replication (10). However, 5hmC may also constitute an epigenetic mark per se.

It is possible to detect and quantify the level of 5hmC present in total genomic DNA by analytical methods that include thin layer chromatography and tandem liquid chromatography-mass spectrometry (2, 11, 12). Mapping the genomic locations of 5hmC has thus far been achieved by enrichment methods that have employed chemistry or antibodies for 5hmC-specific precipitation of DNA fragments that are then sequenced (6-8, 13-15). These pull-down approaches have relatively poor resolution (10s to 100s of nucleotides) and give only relative quantitative information that is likely to be subject to distributional biasing during the enrichment. Quantifiable single nucleotide sequencing of 5mC has been performed using bisulfite sequencing (BS-Seq), which exploits the bisulfite-mediated deamination of cytosine to uracil for which the corresponding transformation of 5mC is much slower (16). However, it has been recognized that both 5mC and 5hmC are very slow to deaminate in the bisulfite reaction and so these two bases cannot be discriminated (17, 18). Two relatively new and elegant single molecule methods have shown promise in detecting 5mC and 5hmC at single nucleotide resolution. Single molecule real-time sequencing (SMRT) has been shown to detect derivatised 5hmC in genomic DNA (19). However, enrichment of DNA fragments containing 5hmC is required, which leads to loss of quantitative information (19). 5mC can be detected, albeit with lower accuracy, by SMRT (19). Furthermore, SMRT has a relatively high rate of sequencing errors (20), the peak calling of modifications is imprecise (19) and the platform has not yet sequenced a whole genome. Protein and solid-state nanopores can resolve 5mC from 5hmC and have the potential to sequence unamplified DNA molecules with further development (21, 22).

The quantitative mapping of 5hmC and 5mC in genomic DNA at single-nucleotide resolution has been reported using "oxidative bisulfite" sequencing (oxBS-Seq) methods (23). These methods involve the specific oxidation of 5hmC to 5fC using potassium perruthenate (KRuO4).

The present inventors have recognised that metal (VI) oxo complexes, such as ruthenate, may be useful in catalysing the selective oxidation of 5hmC residues in polynucleotides to 5fC residues. This may be useful, for example, in methods of "oxidative bisulfite" analysis and sequencing.

An aspect of the invention provides a method of identifying a modified cytosine residue in a sample nucleotide sequence comprising;
(i) providing a population of polynucleotides which comprise the sample nucleotide sequence,
(ii) treating a first portion of said population with a metal (VI) oxo complex,
(iii) treating said first portion of said population and a second portion of said population with bisulfite, and
(iv) identifying the residue in the first and second nucleotide sequences which corresponds to a cytosine residue in the sample nucleotide sequence.

In some embodiments, the residue may be identified by sequencing. For example, a method of identifying a modified cytosine residue in a sample nucleotide sequence may comprise;
(i) providing a population of polynucleotides which comprise the sample nucleotide sequence,
(ii) treating a first portion of said population with a metal (VI) oxo complex,
(iii) treating said first portion of said population and a second portion of said population with bisulfite,
(iv) sequencing the polynucleotides in the first and second portions of the population following steps ii) and iii) to produce first and second nucleotide sequences, respectively and;
(v) identifying the residue in the first and second nucleotide sequences which corresponds to a cytosine residue in the sample nucleotide sequence Suitable sequencing methods are well-known in the art and described in more detail below.

The residues identified in the first and second nucleotide sequences may be indicative of a modified cytosine at the corresponding position in the sample nucleotide sequence i.e. the presence of a modified cytosine at a position in the sample nucleotide sequence may be determined from the identity of the residues which are located at the same position in the first and second nucleotide sequences.

For example, cytosine residues may be present at one or more positions in the sample nucleic acid sequence. The residues at the corresponding positions in the first and second nucleotide sequences may be identified. The presence of a modification, for example a 5-substitution, such as 5-methyl or 5-hydroxymethyl substitution, on a cytosine in the sample nucleotide sequence may be determined from the combination of residues which are identified in the first and second nucleotide sequences respectively (i.e. C and C, U and U, C and U, or U and C) at the position of the cytosine in the sample nucleotide sequence. The cytosine modifications which are indicated by different combinations are shown in table 1.

Treatment with the metal (VI) oxo complex oxidises 5-hydroxymethylcytosine (5hmC) residues in the first portion of polynucleotides into 5-formylcytosine (5fC) residues. 5fC residues in the first portion of polynucleotides are subsequently converted into uracil by the bisulfite treatment of step (iii). In some embodiments, treatment with the metal (VI) oxo complex may further oxidise some or all of the 5-formylcytosine (5fC) residues into 5-carboxylcytosine (5caC) residues. 5caC residues in the first portion of polynucleotides are also converted into uracil by the bisulfite treatment of step (iii).

A metal (VI) oxo complex comprises a metal atom (M) in the +6 oxidation state coordinated with one or more oxygen atoms.

The metal (VI) atom may be tri- or tetra coordinated i.e. the M6+ atom may be coordinated with three oxygen atoms (e.g. rhenium oxide Rh(VI)O$_3$)) or four oxygen atoms in an oxyanion (e.g. ruthenate Ru(VI)O$_4^{2-}$).

In preferred embodiments, the metal (VI) atom is coordinated with four oxygen atoms (MO$_4^{2-}$) in an oxyanion, preferably with tetrahedral geometry. Suitable metal (VI) oxo complexes include manganate (Mn(VI)O$_4^{2-}$), ferrate (Fe(VI)O$_4^{2-}$), osmate (Os(VI)O$_4^{2-}$), ruthenate (Ru(VI)O$_4^{2-}$), or molybate (Mo(VI)O$_4^{2-}$).

In some preferred embodiments, the metal (VI) oxo complex is ruthenate (Ru(VI)O$_4^{2-}$) or manganate (Mn(VI)O$_4^{2-}$), most preferably ruthenate (Ru(VI)O$_4^{2-}$).

Metal (VI) oxo complexes may be prepared by any suitable technique and various methods are available in the art.

For example, a metal (VI) oxo complex (M(VI)O$_4^{2-}$) suitable for use in the oxidation of hmC may be produced by reduction of the corresponding metal (VII) oxo complex or metal (VIII) oxo complex (e.g. M(VII)O$_4^-$ or M(VIII)O$_4$). Any suitable reduction protocol may be employed, for example heating or treatment with hydroxide or peroxide ions. Suitable metal (VI) oxo complexes (M(VI)O$_4^{2-}$) may also be produced by oxidation of metal oxides and oxo complexes (e.g. MO$_2$)

Ruthenate (Ru(VI)O$_4^{2-}$) may be conveniently prepared by reducing perruthenate (Ru(VII)O$_4^-$) or ruthenium tetroxide (Ru(VIII)O$_4$), for example using iodide, hydroxide (OH$^-$), peroxide (O$_2^{2-}$) or by heating. Ruthenate may also be conveniently prepared by oxidisation of Ru complexes, for example using KMnO$_4$ or HClO (hypochlorite). Ruthenate (Ru(VI)O$_4^{2-}$ may also be prepared from ruthenium trioxide (RuO$_3$), for example using aqueous base and persulfate.

Manganate (Mn(VI)O$_4^{2-}$) may be conveniently prepared by reducing permanganate (Mn(VII)O$_4^-$) using hydroxide (OH$^-$), peroxide (O$_2^{2-}$) or by heating.

Osmate ([Os(VI)O$_4$(OH)$_2$]$^{2-}$) may be prepared by reducing Os(VIII)O$_4$ using hydroxide (Os(VIII)O$_4$+2OH$^-$→[Os(VI)O$_4$(OH)$_4$]$^{2-}$).

Ferrate (Fe(VI)O$_4^{2-}$) may be prepared by heating iron filings with potassium nitrate$^-$; heating iron(III) hydroxide with hypochlorite in alkaline conditions; or by alkaline hypochlorite oxidation of ferric nitrate.

Molybdate (MoO$_4^{2-}$) may be prepared by dissolving molybdenum trioxide in alkali (MoO$_3$+2NaOH→Na$_2$MoO$_4$.2H$_2$O)

Examples of suitable methods for the preparation of ruthenate (VI) oxo complexes and manganate (VI) oxo complexes are described in more detail below.

Metal (VI) oxo complexes may also be obtained from commercial sources (e.g. Alfa Aesar, MA USA; Sigma Aldrich, USA).

Treatment with the metal (VI) oxo complex selectively oxidises 5-hydroxymethylcytosine residues in first portion of the population of polynucleotides into 5-formylcytosine residues. Substantially no other functionality in the polynucleotide is oxidised by the metal (VI) oxo complex. The treatment therefore does not result in the reaction of any thymine or 5-methylcytosine residues, where such are present.

The first portion of polynucleotides may be treated with the metal (VI) oxo complex at a sufficient concentration to selective oxidise 5-hydroxymethylcytosine residues in the polynucleotides. Suitable concentrations of the metal (VI) oxo complex for the selective oxidisation of 5-hydroxymethylcytosine may be readily determined using standard techniques. For example, 0.1 mM to 10 mM and most preferably about 1 mM ruthenate may be employed.

Typically, metal (VI) oxo complexes for use in the methods described herein are stored in concentrated stock solutions, which may for example have a concentration which is 5 fold, 10 fold, 100 fold, 150 fold or 500 fold greater than the concentration used to treat the first portion of polynucleotides. A typical stock solution may be 100 mM to 150 mM.

Oxidation of hmC residues by the metal (VI) oxo complex does not degrade or damage the polynucleotides in the first portion to an extent which prevents subsequent amplification and/or sequencing of the first portion i.e. the first portion includes sufficient intact or undamaged polynucleotides following treatment with the metal (VI) oxo complex to allow amplification and/or sequencing and is not totally degraded.

Preferably, the metal (VI) oxo complex causes no degradation or damage, or minimal degradation or damage to the polynucleotides in the first portion or does not cause substantial degradation or damage to the polynucleotides.

Polynucleotide damage or degradation may include phosphodiester bond cleavage; 5' dephosphorylation and/or depurination. Treatment with the metal (VI) oxo complex may not cause substantial phosphodiester bond cleavage; 5' dephosphorylation; depyrimidination and/or depurination of the polynucleotides in the first portion and, preferably causes minimal or no phosphodiester bond cleavage; 5' dephosphorylation and/or depurination.

Treatment with the metal (VI) oxo complex may result in the formation of some corresponding 5-carboxycytosine product as well as 5-formylcytosine. The formation of this product does not negatively impact on the methods of identification described herein. Under the bisulfite reaction conditions that are used to convert 5-formylcytosine to uracil, 5-carboxycytosine is observed to convert to uracil also. It is understood that a reference to 5-formylcytosine that is obtained by oxidation of 5-hydroxymethylcytosine may be a reference to a product also comprising 5-carboxycytosine that is also obtained by that oxidization.

Advantageously, the treatment conditions may also preserve the polynucleotides in a denatured state i.e. denaturing conditions may be employed. Suitable conditions cause denaturation of the polynucleotides without causing damage or degradation. For example, the polynucleotides may be treated with the metal (VI) oxo complex under alkali conditions, such as 50 mM to 500 mM NaOH or 50 mM to 500 mM KOH.

Following treatment with the metal (VI) oxo complex, the polynucleotides in the first portion may be purified. Purification may be performed using any convenient nucleic acid purification technique.

Suitable nucleic acid purification techniques include spin-column chromatography.

The polynucleotides may be subjected to further, repeat treatment with the metal (VI) oxo complex. Such steps are undertaken to maximise the conversion of 5-hydroxycytosine to 5-formylcytosine. This may be necessary where a polynucleotide has sufficient secondary structure that is capable of re-annealing. Any annealed portions of the polynucleotide may limit or prevent access of the metal (VI) oxo complex to that portion of the structure, which has the effect of protecting 5-hydroxycytosine from oxidation.

In some embodiments, the first portion of the population of polynucleotides may for example be subjected to multiple cycles of treatment with the metal (VI) oxo complex followed by purification. For example, one, two, three or more than three cycles may be performed.

Following treatment with the metal (VI) oxo complex and optional purification, the first portion of the population is then treated with bisulfite. A second portion of the population which has not been oxidised is also treated with bisulfite.

Bisulfite treatment converts both cytosine and 5-formylcytosine residues in a polynucleotide into uracil. As noted above, where any 5-carboxycytosine is present (as a product of the oxidation step), this 5-carboxycytosine is converted into uracil in the bisulfite treatment. Without wishing to be bound by theory, it is believed that the reaction of the 5-formylcytosine proceeds via loss of the formyl group to yield cytosine, followed by a subsequent deamination to give uracil. The 5-carboxycytosine is believed to yield the uracil through a sequence of decarboxylation and deamination steps. Bisulfite treatment may be performed under conditions that convert both cytosine and 5-formylcytosine or 5-carboxycytosine residues in a polynucleotide as described herein into uracil.

Polynucleotides may be treated with bisulfite by incubation with bisulfite ions ($HSO_3^{2-}$). The use of bisulfite ions ($HSO_3^{2-}$) to convert unmethylated cytosines in nucleic acids into uracil is standard in the art and suitable reagents and conditions are well known to the skilled person (52-55). Numerous suitable protocols and reagents are also commercially available (for example, EpiTect™, Qiagen NL; EZ DNA Methylation™ Zymo Research Corp CA; CpGenome Turbo Bisulfite Modification Kit; Millipore).

A feature of OxBS methods is the conversion of unmethylated cytosine (which may be generated in situ from 5-formylcytosine or 5-carboxycytosine) to uracil. This reaction is typically achieved through the use of bisulfite. However, in general aspects of the invention, any reagent or reaction conditions may be used to effect the conversion of cytosine to uracil. Such reagents and conditions are selected such that little or no 5-methylcytosine reacts, and more specifically such that little or no 5-methylcytosine reacts to form uracil. The reagent, or optionally a further reagent, may also effect the conversion of 5-formylcytosine or 5-carboxycytosine to cytosine or uracil.

Following the incubation with bisulfite ions, the portions of polynucleotides may be immobilised, washed, desulfonated, eluted and/or otherwise treated as required.

Methods using metal (VI) oxo complexes as described herein may be useful in identifying and/or distinguishing cytosine (C), 5-methylcytosine (5mC), 5-hydroxymethylcytosine (5hmC) in a sample nucleotide sequence. For example, the methods may be useful in distinguishing one residue from the group consisting of cytosine (C), 5-methylcytosine (5mC) and 5-hydroxymethylcytosine (5hmC) from the other residues in the group.

Preferably, modified cytosine residues, such as 5-hydroxymethylcytosine, in the first portion of said population are not labelled, for example with substituent groups, such as glucose, before the oxidisation or reduction of step ii).

The identification of a residue at a position in one or both of the first and second nucleotide sequences as cytosine in one or both of first and second nucleotide sequences is indicative that the cytosine residue at that position in the sample nucleotide sequence is 5-methylcytosine or 5-hydroxymethylcytosine.

5-hydroxymethylcytosine (5hmC) may be identified in the sample nucleotide sequence. A uracil residue at a position in the first nucleotide sequence which corresponds to a cytosine in the sample nucleotide sequence and a cytosine at the same position in the second nucleotide sequence are indicative that the cytosine residue at that position in the sample nucleotide sequence is 5-hydroxylmethylcytosine (5hmC).

A method of identifying a 5-hydroxymethylcytosine (5hmC) residue in a sample nucleotide sequence or distinguishing 5-hydroxymethylcytosine from cytosine (C), 5-methylcytosine, and 5-formylcytosine (5fC) in a sample nucleotide sequence may comprise;
(i) providing a population of polynucleotides which comprise the sample nucleotide sequence,
(ii) treating the first portion of said population with a metal (VI) oxo complex,
(iii) further treating said first portion of said population and a second portion of said population with bisulfite, and;
(iv) identifying the residue in the first and second portions of said population at the same position as a cytosine residue in the sample nucleotide sequence,
wherein the presence of a uracil residue in the first portion and a cytosine in the second portion is indicative that the cytosine residue in the sample nucleotide sequence is 5-hydroxylmethylcytosine.

For example, a method of identifying a 5-hydroxymethylcytosine (5hmC) residue in a sample nucleotide sequence or distinguishing 5-hydroxymethylcytosine from cytosine (C), 5-methylcytosine, and 5-formylcytosine (5fC) in a sample nucleotide sequence may comprise;
(i) providing a population of polynucleotides which comprise the sample nucleotide sequence,
(ii) treating the first portion of said population with a metal (VI) oxo complex,
(iii) further treating said first portion of said population and a second portion of said population with bisulfite,
(iv) sequencing the polynucleotides in the first and second portions of the population following steps ii) and iii) to produce first and second nucleotide sequences, respectively and;
(v) identifying the residue in the first and second nucleotide sequences which corresponds to a cytosine residue in the sample nucleotide sequence,
wherein the presence of a uracil residue in the first nucleotide sequence and a cytosine in the second nucleotide sequence is indicative that the cytosine residue in the sample nucleotide sequence is 5-hydroxylmethylcytosine.

5-methylcytosine (5mC) may be identified in a sample nucleotide sequence. Cytosine at a position in both the first and second nucleotide sequences that correspond to a cytosine residue in the sample nucleotide sequence are indicative that the cytosine residue in the sample nucleotide sequence is 5-methylcytosine (5mC).

A method of identifying 5-methylcytosine in a sample nucleotide sequence or distinguishing 5-methylcytosine from cytosine (C), 5-hydroxymethylcytosine (5hmC) and 5-formylcytosine (5fC) in a sample nucleotide sequence may comprise;
(i) providing a population of polynucleotides which comprise the sample nucleotide sequence, (ii) treating the first portion of said population with a metal (VI) oxo complex, (iii) further treating the first portion of said population and a second portion of said population with bisulfite, and (v) identifying the residue in the first and second portions of said population which is at the same position as a cytosine residue in the sample nucleotide sequence wherein the presence of a cytosine in both the first and second portions is indicative that the cytosine residue in the sample nucleotide sequence is 5-methylcytosine (5mC).

For example, a method of identifying 5-methylcytosine in a sample nucleotide sequence or distinguishing 5-methylcytosine from cytosine (C), 5-hydroxymethylcytosine (5hmC) and 5-formylcytosine (5fC) in a sample nucleotide sequence may comprise;

(i) providing a population of polynucleotides which comprise the sample nucleotide sequence, (ii) treating the first portion of said population with a metal (VI) oxo complex, (iii) further treating the first portion of said population and a second portion of said population with bisulfite, (iv) sequencing the polynucleotides in the first and second portions of the population following steps ii) and iii) to produce first and second nucleotide sequences, respectively and;

(v) identifying the residue in the first and second nucleotide sequences which corresponds to a cytosine residue in the sample nucleotide sequence wherein the presence of a cytosine in both the first and second nucleotide sequences is indicative that the cytosine residue in the sample nucleotide sequence is 5-methylcytosine (5mC).

Uracil residues at a position in both the first and second nucleotide sequences which correspond to a cytosine in the sample nucleotide sequence are indicative that the cytosine residue in the sample nucleotide sequence is not 5-methylcytosine or 5-hydroxymethylcytosine i.e. the cytosine residue is unmodified cytosine or 5-formylcytosine.

A summary of the cytosine modifications at a position in the sample nucleotide sequence which are indicated by specific combinations of cytosine and uracil at the position in the first and second nucleotide sequences is shown in Table 1.

The first and second portions of the polynucleotide population may be treated with bisulfite and/or sequenced simultaneously or sequentially.

In some embodiments, treatment of the second portion may not be required to identity or distinguish a modified cytosine residue in the sample nucleotide sequence. For example, Table 1 shows that oxidation and bisulfite treatment of the first portion of the polynucleotide population is sufficient to identify 5-methylcytosine in the sample nucleotide sequence. A method of identifying 5-methylcytosine in a sample nucleotide sequence or distinguishing 5-methylcytosine from cytosine (C), 5-hydroxymethylcytosine (5hmC) and 5-formylcytosine (5fC) in a sample nucleotide sequence may comprise;

(i) providing a population of polynucleotides which comprise the sample nucleotide sequence, (ii) treating the first portion of said population with a metal (VI) oxo complex, (iii) further treating the first portion of polynucleotides with bisulfite, (iv) identifying the residue in the treated first portion of polynucleotides which is at the same position as a cytosine residue in the sample nucleotide sequence (i.e.

the residue in the first portion which corresponds to the cytosine residue in the sample nucleotide sequence), wherein the presence of a cytosine at the position in the treated first portion is indicative that the cytosine residue in the sample nucleotide sequence is 5-methylcytosine (5mC).

For example, a method of identifying 5-methylcytosine in a sample nucleotide sequence or distinguishing 5-methylcytosine from cytosine (C), 5-hydroxymethylcytosine (5hmC) and 5-formylcytosine (5fC) in a sample nucleotide sequence may comprise;

(i) providing a population of polynucleotides which comprise the sample nucleotide sequence, (ii) treating the first portion of said population with a metal (VI) oxo complex, (iii) further treating the first portion of polynucleotides with bisulfite, (iv) sequencing the polynucleotides in the population following steps ii) and iii) to produce a treated nucleotide sequence, and;

(v) identifying the residue in the treated nucleotide sequence which corresponds to a cytosine residue in the sample nucleotide sequence, wherein the presence of a cytosine in the treated nucleotide sequence is indicative that the cytosine residue in the sample nucleotide sequence is 5-methylcytosine (5mC).

In some embodiments, methods according to any one of the aspects and embodiments set out above may comprise sequencing a first portion of polynucleotides which has been oxidised and bisulfite treated; and a second portion of polynucleotides which has been bisulfite treated. For example, a method may comprise;

(i) providing a population of polynucleotides which comprise the sample nucleotide sequence, (ii) providing first and second portions of the population, (iii) treating the first portion of said population with a metal (VI) oxo complex, (iv) treating the first and second portions of said population with bisulfite, (v) sequencing the polynucleotides in the first and second portions of the population following steps ii), iii) and iv) to produce first and second nucleotide sequences, respectively and;

(vi) identifying the residue in the first and second nucleotide sequences which corresponds to a cytosine residue in the sample nucleotide sequence.

The sample nucleotide sequence may be already known or it may be determined. The sample nucleotide sequence is the sequence of untreated polynucleotides in the population i.e. polynucleotides which have not been oxidised, reduced or bisulfite treated. In the sample nucleotide sequence, modified cytosines are not distinguished from cytosine. 5-Methylcytosine, 5-formylcytosine and 5-hydroxymethylcytosine are all indicated to be or identified as cytosine residues in the sample nucleotide sequence. For example, methods according to any one of the aspects and embodiments set out above may further comprise;

providing a third portion of the population of polynucleotides comprising sample nucleotide sequence; and, sequencing the polynucleotides in the third portion to produce the sample nucleotide sequence.

The sequence of the polynucleotides in the third portion may be determined by any appropriate sequencing technique.

The positions of one or more cytosine residues in the sample nucleotide sequence may be determined. This may be done by standard sequence analysis. Since modified cytosines are not distinguished from cytosine, cytosine residues in the sample nucleotide sequence may be cytosine, 5-methylcytosine, 5-formylcytosine or 5-hydroxymethylcytosine.

The first and second nucleotide sequences (i.e. the nucleotide sequences of the first and second portions) may be compared to the sample nucleotide sequence. For example, the residues at positions in the first and second sequences corresponding to the one or more cytosine residues in the sample nucleotide sequence may be identified.

In some embodiments, the residue in the first and second portions which is at the same position as a cytosine residue in the sample nucleotide sequence may be identified.

The modification of a cytosine residue in the sample nucleotide sequence may be determined from the identity of the nucleotides at the corresponding positions in the first and second nucleotide sequences (i.e. the nucleotides in the same position as the cytosine residue in the nucleotide sequences of the first and second portions).

The polynucleotides in the population all contain the same sample nucleotide sequence i.e. the sample nucleotide sequence is identical in all of the polynucleotides in the population.

The effect of different treatments on cytosine residues within the sample nucleotide sequence can then be determined, as described herein.

The sample nucleotide sequence may be a genomic sequence. For example, the sequence may comprise all or part of the sequence of a gene, including exons, introns or upstream or downstream regulatory elements, or the sequence may comprise genomic sequence that is not associated with a gene. In some embodiments, the sample nucleotide sequence may comprise one or more CpG islands.

Suitable polynucleotides include DNA, preferably genomic DNA, and/or RNA, such as genomic RNA (e.g. mammalian, plant or viral genomic RNA), mRNA, tRNA, rRNA and non-coding RNA.

The polynucleotides comprising the sample nucleotide sequence may be obtained or isolated from a sample of cells, for example, mammalian cells, preferably human cells.

Suitable samples include isolated cells and tissue samples, such as biopsies.

Modified cytosine residues including 5hmC and 5fC have been detected in a range of cell types including embryonic stem cells (ESCS) and neural cells (2, 3, 11, 45, 46).

Suitable cells include somatic and germ-line cells.

Suitable cells may be at any stage of development, including fully or partially differentiated cells or non-differentiated or pluripotent cells, including stem cells, such as adult or somatic stem cells, foetal stem cells or embryonic stem cells.

Suitable cells also include induced pluripotent stem cells (iPSCs), which may be derived from any type of somatic cell in accordance with standard techniques.

For example, polynucleotides comprising the sample nucleotide sequence may be obtained or isolated from neural cells, including neurons and glial cells, contractile muscle cells, smooth muscle cells, liver cells, hormone synthesising cells, sebaceous cells, pancreatic islet cells, adrenal cortex cells, fibroblasts, keratinocytes, endothelial and urothelial cells, osteocytes, and chondrocytes.

Suitable cells include disease-associated cells, for example cancer cells, such as carcinoma, sarcoma, lymphoma, blastoma or germ line tumour cells.

Suitable cells include cells with the genotype of a genetic disorder such as Huntington's disease, cystic fibrosis, sickle cell disease, phenylketonuria, Down syndrome or Marfan syndrome.

Methods of extracting and isolating genomic DNA and RNA from samples of cells are well-known in the art. For example, genomic DNA or RNA may be isolated using any convenient isolation technique, such as phenol/chloroform extraction and alcohol precipitation, caesium chloride density gradient centrifugation, solid-phase anion-exchange chromatography and silica gel-based techniques.

In some embodiments, whole genomic DNA and/or RNA isolated from cells may be used directly as a population of polynucleotides as described herein after isolation. In other embodiments, the isolated genomic DNA and/or RNA may be subjected to further preparation steps.

The genomic DNA and/or RNA may be fragmented, for example by sonication, shearing or endonuclease digestion, to produce genomic DNA fragments. A fraction of the genomic DNA and/or RNA may be used as described herein. Suitable fractions of genomic DNA and/or RNA may be based on size or other criteria. In some embodiments, a fraction of genomic DNA and/or RNA fragments which is enriched for CpG islands (CGIs) may be used as described herein.

The genomic DNA and/or RNA may be denatured, for example by heating or treatment with a denaturing agent. Suitable methods for the denaturation of genomic DNA and RNA are well known in the art.

In methods according to any one of the aspects and embodiments set out above, the genomic DNA and/or RNA may be adapted for sequencing and/or other analysis before oxidation and bisulfite treatment, or bisulfite treatment alone. The nature of the adaptations depends on the sequencing or analysis method that is to be employed. For example, for some sequencing methods, primers may be ligated to the free ends of the genomic DNA and/or RNA fragments following fragmentation. Suitable primers may contain 5mC to prevent the primer sequences from altering during oxidation and bisulfite treatment, or bisulfite treatment alone, as described herein. In other embodiments, the genomic DNA and/or RNA may be adapted for sequencing after oxidation and/or bisulfite treatment, as described herein.

Following fractionation, denaturation, adaptation and/or other preparation steps, the genomic DNA and/or RNA may be purified by any convenient technique.

Following preparation, the population of polynucleotides may be provided in a suitable form for further treatment as described herein. For example, the population of polynucleotides may be in aqueous solution in the absence of buffers before treatment as described herein.

Polynucleotides for use as described herein may be single or double-stranded.

The population of polynucleotides may be divided into two, three, four or more separate portions, each of which contains polynucleotides comprising the sample nucleotide sequence. These portions may be independently treated and sequenced as described herein.

Preferably, the portions of polynucleotides are not treated to add labels or substituent groups, such as glucose, to 5-hydroxymethylcytosine residues in the sample nucleotide sequence before oxidation and/or reduction.

In methods according to any one of the aspects and embodiments set out above, the first and second portions of polynucleotides from the population may be amplified following treatment as described above. This may facilitate further manipulation and/or sequencing. Sequence alterations in the first and second portions of polynucleotides are preserved following the amplification. Suitable polynucleotide amplification techniques are well known in the art and include PCR. The presence of a uracil (U) residue at a position in the first and/or second portions of polynucleotide may be indicated or identified by the presence of a thymine (T) residue at that position in the corresponding amplified polynucleotide. Optionally, the portions of polynucleotides may be purified before amplification.

As described above, the residue in the first and second portions of polynucleotides at the same position as the cytosine residue in the sample nucleotide sequence may be identified by sequencing the polynucleotides in the first and second portions of the population following steps ii) and iii) to produce first and second nucleotide sequences, respectively. Polynucleotides may be adapted after oxidation, reduction and/or bisulfite treatment to be compatible with a sequencing technique or platform. The nature of the adaptation will depend on the sequencing technique or platform. For example, for Solexa-Illumina sequencing, the treated polynucleotides may be fragmented, for example by sonication or restriction endonuclease treatment, the free ends of the polynucleotides repaired as required, and primers ligated onto the ends.

Polynucleotides may be sequenced using any convenient low or high throughput sequencing technique or platform, including Sanger sequencing (38), Solexa-Illumina sequencing (39), Ligation-based sequencing (SOLiD™) (40), pyrosequencing (41); Single Molecule Real Time sequencing (SMRT™) (42, 43); and semiconductor array sequencing (Ion Torrent™) (44).

Suitable protocols, reagents and apparatus for polynucleotide sequencing are well known in the art and are available commercially.

The residue in the first and second portions of polynucleotides at the same position as the cytosine residue in the sample nucleotide sequence may be identified by hybridisation-based techniques.

In some embodiments, the residue may be identified using specific oligonucleotide probes which hybridise to the polynucleotides with cytosine at the same position as the cytosine residue in the sample nucleotide sequence but do not hybridise to polynucleotides with any other residue at this position; or which hybridise to the polynucleotides with a uracil (or thymine) at the same position as the cytosine residue in the sample nucleotide sequence but do not hybridise to polynucleotides with any other residue at the position. For example, the residue in the first and second portions may be identified by;
 a) contacting polynucleotides of the first and second portions of the population with a detection oligonucleotide,
  wherein the detection oligonucleotide specifically hybridises to only one of i) polynucleotides of said portions which have a cytosine at the same position as the cytosine residue in the sample nucleotide sequence and ii) polynucleotides of said portions which have a uracil at the same position as the cytosine residue in the sample nucleotide sequence and;
 b) determining the hybridisation of the detection oligonucleotide to the polynucleotides of the first and second portions.

The presence or amount of hybridisation of the detection oligonucleotide to the polynucleotides is indicative of the identity of the residue in the first and second portions of said population which corresponds to the cytosine residue in the sample nucleotide sequence.

In some embodiments, two or more detection oligonucleotides may be employed. For example, a method may comprise contacting polynucleotides of the first and second portions of the population with;
 i) a first detection oligonucleotide which specifically hybridises to polynucleotides of said portions which have a cytosine at the same position as the cytosine residue in the sample nucleotide sequence, and;
 ii) a second detection oligonucleotide which specifically hybridises to polynucleotides of said portions which have a uracil at the same position as the cytosine residue in the sample nucleotide sequence, and;
 b) determining the hybridisation of the first and second detection oligonucleotides to the polynucleotides of the first and second portions,
 wherein the presence or amount of hybridisation of the first and second detection oligonucleotide is indicative of the identity of the residue in the first and second portions of said population at the same position as the cytosine residue in the sample nucleotide sequence. For example, hybridisation of the first but not the second detection oligonucleotide is indicative that the residue is cytosine and hybridisation of the second but not the first detection oligonucleotide is indicative that the residue is uracil.

Suitable protocols, reagents and apparatus for the identification of nucleotide residues by hybridisation are well known in the art and are available commercially. Suitable techniques include dynamic allele specific hybridisation (26), molecular beacons (27), array-based techniques (28) and Taqman™ (36).

In some embodiments, the residue in the first and second portions may be identified using oligonucleotide probes which hybridise to the polynucleotides of the first and second portions. Following hybridisation, the presence or absence of a base mismatch between the probe and the polynucleotide at the position in the polynucleotides which corresponds to the cytosine residue in the sample nucleotide sequence may be determined. For example, the residue in the first and second portions may be identified by;
 a) contacting polynucleotides of the first and second portions of the population with a detection oligonucleotide which specifically hybridises to the polynucleotides, and;
 b) determining the presence or absence of a base mismatch between the detection oligonucleotide and the polynucleotides at the position of the cytosine residue in the sample nucleotide sequence.

Base mismatches may be determined by any suitable technique. Suitable protocols, reagents and apparatus for the identification of base mismatches are well-known in the art and include Flap endonuclease and Invader assays (32), primer extension assays (28), oligonucleotide ligation assays (28, 37), denaturing high-performance liquid chromatography (DHPLC) and mismatch-specific endonuclease cleavage (47, 49, 50, 51).

In some embodiments, primer extension techniques may be employed to identify the residue in the first and second portions of polynucleotides which is at the same position as the cytosine residue in the sample nucleotide sequence. For example, a method may comprise;
 a) contacting polynucleotides of the first and second portions of the population with a detection oligonucleotide which hybridises to the polynucleotides immediately 3' of the position of the cytosine residue in the sample nucleotide sequence, b) extending the hybridised detection oligonucleotide to incorporate a nucleotide which is complementary to the residue in the polynucleotides which is at the same position as the cytosine residue in the sample nucleotide sequence, and c) determining the identity of the incorporated nucleotide.

Suitable protocols, reagents and apparatus for use in primer extension assays are well-known in the art and include Infinium HD (Illumina; 33) and arrayed primer extension (APEX) (28, 34, 35).

In some embodiments, specific amplification techniques may be employed to identify the residue in the first and second portions of polynucleotides which corresponds to a cytosine residue in the sample nucleotide sequence. The polynucleotides of the first and second portions may be amplified using amplification primers which produce an amplification product only when a cytosine residue is present at the same position in the polynucleotides as the cytosine residue in the sample sequence and not when another residue is present at this position; or which produce an amplification product only when a uracil residue is present at the same position in the polynucleotides as the cytosine residue in the sample sequence and not when another residue is present at this position. For example, a method may comprise;

a) subjecting the first and second portions of the population to amplification with one or more amplification primers which either;

i) amplify polynucleotides in said portions which have a cytosine at the position corresponding to the cytosine residue in the sample sequence to produce an amplification product and do not amplify polynucleotides in said portions with other bases at this position; or.

ii) amplify polynucleotides in said portions which have a uracil at the position corresponding to the cytosine residue in the sample sequence to produce an amplification product and do not amplify polynucleotides in said portions with other bases at this position, and;

b) determining the presence of an amplification product produced by said amplification primers.

Suitable amplification techniques are well known in the art and include PCR based techniques such as amplification refractory mutation system (ARMS)-PCR (29), allele-specific PCR (30), allele specific amplification (ASA; 31) and adaptor-ligation-mediated ASA (48).

In any of the methods described above, the detection oligonucleotide(s) and/or amplification primers may be immobilised, for example on beads or an array.

Other suitable techniques for identifying the residue in the first and second portions of polynucleotides which is at the same position as the cytosine residue in the sample nucleotide sequence may be employed. For example, a method may comprise;

a) fragmenting the polynucleotides of first and second portions to produce fragments of the first and second portions, b) determining the size and/or mass of the fragments and c) determining from the size and mass of the fragments of the first and second populations the identity of the residue in the first and second nucleotide sequences.

The polynucleotides may be fragmented by any suitable method, including base-specific endonuclease techniques (47, 49, 50, 51). Suitable methods for determining the size and/or mass of the polynucleotide fragments are also well-known in the art and include MALDI-MS.

Suitable protocols, reagents and apparatus for use in fragmentation and detection techniques are well-known in the art and include iPLEX SNP genotyping (Sequenom) (24, 25).

In other embodiments, the residue in the first and second portions of polynucleotides at the same position as the cytosine residue in the sample nucleotide sequence may be identified using one or both of i) a specific binding member which binds to polynucleotides of said portions which have a cytosine at the same position as the cytosine residue in the sample nucleotide sequence and does not bind to polynucleotides of said portions which do not have a cytosine at this position; and (ii) a specific binding member which binds to polynucleotides of said portions which have a uracil at the same position as the cytosine residue in the sample nucleotide sequence and does not bind to polynucleotides of said portions which do not have a uracil at this position.

The specific binding member may be contacted with the first and second portions of polynucleotides and the binding of the member to the polynucleotides determined. The presence of binding may be indicative of the identity of the residue in the first and second portions of polynucleotides which is located at the same position as the cytosine residue in the sample nucleotide sequence.

Suitable specific binding members are well-known in the art and include antibody molecules, such as whole antibodies and fragments, and aptamers.

The residues at positions in the first and second nucleotide sequences which correspond to cytosine in the sample nucleotide sequence may be identified.

The modification of a cytosine residue at a position in the sample nucleotide sequence may be determined from the identity of the residues at the corresponding positions in the first and second nucleotide sequences, as described above.

The extent or amount of cytosine modification in the sample nucleotide sequence may be determined. For example, the proportion or amount of 5-hydroxymethylcytosine and/or 5-methylcytosine in the sample nucleotide sequence compared to unmodified cytosine may be determined.

In methods according to any one of the aspects and embodiments set out above, polynucleotides, for example the population of polynucleotides or 1, 2 or all 3 of the first, second and third portions of the population, may be immobilised on a solid support.

Similarly, detection oligonucleotides, amplification primers and specific binding members may be immobilised on a solid support.

A solid support is an insoluble, non-gelatinous body which presents a surface on which the polynucleotides can be immobilised.

Examples of suitable supports include glass slides, microwells, membranes, or microbeads. The support may be in particulate or solid form, including for example a plate, a test tube, bead, a ball, filter, fabric, polymer or a membrane. Polynucleotides may, for example, be fixed to an inert polymer, a 96-well plate, other device, apparatus or material which is used in nucleic acid sequencing or other investigative context. The immobilisation of polynucleotides to the surface of solid supports is well-known in the art. In some embodiments, the solid support itself may be immobilised. For example, microbeads may be immobilised on a second solid surface.

In some preferred embodiments, the first, second and/or third polynucleotides may be immobilised on magnetic beads. This may facilitate purification of the polynucleotides between steps.

In methods according to any one of the aspects and embodiments set out above, the first, second and/or third portions of the population of polynucleotides may be amplified before sequencing or other analysis. Preferably, the portions of polynucleotide are amplified following the treatment with bisulfite.

Suitable methods for the amplification of polynucleotides are well known in the art.

Following amplification, the amplified portions of the population of polynucleotides may be sequenced or otherwise analysed. In some embodiments, specific amplification primers may be employed, such that the presence or absence of amplified portions is in itself indicative of the identity of the residue in the portion of polynucleotides which is located at the same position as the cytosine residue in the sample nucleotide sequence.

Nucleotide sequences may be compared and the residues at positions in the first, second and/or third nucleotide sequences which correspond to cytosine in the sample nucleotide sequence may be identified, using computer-based sequence analysis.

Nucleotide sequences, such as CpG islands, with cytosine modification greater than a threshold value may be identified. For example, one or more nucleotide sequences in which greater than 1%, greater than 2%, greater than 3%, greater than 4% or greater than 5% of cytosines are hydroxymethylated may be identified.

Computer-based sequence analysis may be performed using any convenient computer system and software.

Another aspect of the invention provides a kit for use in a method of identifying a modified cytosine residue according to any one of the aspects and embodiments set out above, in particular a 5-methylcytosine (5mC) or 5-hydroxymethylcytosine (5hmC), comprising;
(i) a metal (VI) oxo complex; and,
(ii) a bisulfite reagent.

Suitable metal (VI) oxo complexes and bisulfite reagents are described above. For example, the metal (VI) oxo complex may be manganate ($MnO_4^{2-}$), ferrate ($FeO_4^{2-}$), osmate ($OsO_4^{2-}$), ruthenate ($RuO_4^2$), or molybdate oxyanion ($MoO_4^{2-}$).

In some preferred embodiments, the metal (VI) oxo complex is ruthenate ($RuO_4^{2-}$) or manganate ($MnO_4^{2-}$), preferably, ruthenate ($RuO_4^{2-}$).

The metal (VI) oxo complex may be supplied in the form of a salt, for example an alkali metal salt, such as lithium, sodium or potassium salt. Preferably the metal (VI) oxo complex is supplied in the form of a potassium salt.

In some preferred embodiments, the kit may comprise dipotassium ruthenate ($K_2RuO_4$) or dipotassium manganate ($K_2MnO_4$).

The metal (VI) oxo complex or salt thereof may be supplied in the form of a solution, preferably an aqueous solution.

The solution may be a concentrated solution for dilution to the appropriate working concentration at the time of performing the polynucleotide treatment.

A suitable metal (VI) oxo complex solution may have a concentration which is at least 2 fold greater than the working concentration, for example 2 fold to 100 fold greater, preferably about 10 fold greater. For example, the concentrated solution may comprise 0.1 mM to 10M, 1 mM to 1M, or 5 mM to 20 mM metal (VI) oxo complex, preferably about 10 mM.

Preferably, the concentrated metal (VI) oxo complex solution is alkaline. For example, the solution may have a pH of 8 to 14. A suitable solution may comprise 0.5M to 5M $OH^-$. For example, the metal (VI) oxo complex may be dissolved in 0.5M to 5M NaOH or KOH.

The bisulfite reagent may be ammonium bisulfite ($NH_4HSO_3$) or sodium bisulfite ($NaHSO_3$). The bisulfite reagent may be in the form of a solution. For example, the kit may comprise a 1M to 10M solution of $NH_4HSO_3$ or $NaHSO_3$.

A kit may further comprise a population of control polynucleotides comprising one or more modified cytosine residues, for example 5-methylcytosine (5mC) or 5-hydroxymethylcytosine (5hmC). In some embodiments, the population of control polynucleotides may be divided into one or more portions, each portion comprising a different modified cytosine residue.

A kit for use in identifying modified cytosines may include one or more articles and/or reagents for performance of the method, such as means for providing the test sample itself, including DNA and/or RNA isolation and purification reagents, and sample handling containers (such components generally being sterile).

For example, the kit may further comprise sample preparation reagents for the isolation and extraction of genomic DNA or RNA from a cell. Suitable reagents are well known in the art and include solid-phase anion-exchange chromatography reagents and devices.

A kit may further comprise adaptors or primers for ligation to the termini of the population of polynucleotides following fragmentation. The nature of the adaptors or primers depends on the sequencing method being used. Suitable primers may contain 5mC to prevent the primer sequences from altering during oxidation and bisulfite treatment, or bisulfite treatment alone, as described herein. In some embodiments, the adaptors or primers may comprise a label, such as biotin, to facilitate immobilisation of the polynucleotides.

A kit may further comprise detection oligonucleotides and/or amplification primers for the identification of the residue at a position which corresponds to a cytosine in the sample nucleotide sequence. The oligonucleotides and/or primers may comprise a label, such as biotin, to facilitate detection and/or immobilisation.

The kit may further comprise purification devices and reagents for isolating and/or purifying a portion of polynucleotides, following treatment as described herein. Suitable reagents are well known in the art and include gel filtration columns and washing buffers.

The kit may further comprise amplification reagents for amplification, preferably PCR amplification, of the first, second and/or third portions of the population, following treatment as described herein. Suitable amplification reagents are well known in the art and include oligonucleotide primers, nucleotides, buffers and/or polymerases.

In some embodiments, the kit may further comprise magnetic beads for immobilisation of one or more portions of polynucleotides. The magnetic beads may be coated with a specific binding member, such as streptavidin, for attachment of the polynucleotides.

The kit may include instructions for use in a method of identifying a modified cytosine residue as described above.

A kit may include one or more other reagents required for the method, such as buffer solutions, sequencing and other reagents.

Methods and kits for OxBS sequencing are described in Booth et al (2012) Science 336 934 and PCT/GB2012/051819, which are incorporated herein by reference in their entirety for all purposes.

Various further aspects and embodiments of the present invention will be apparent to those skilled in the art in view of the present disclosure.

All documents mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to any one of the aspects and embodiments that are described above.

Certain aspects and embodiments of the invention will now be illustrated by way of example and with reference to the figures described below.

FIG. 1 shows the oxidative bisulfite reaction scheme of the invention: treatment with metal (VI) oxo complex oxidises 5hmC to 5fC and then bisulfite treatment and NaOH convert 5fC to U. The R group is DNA.

FIG. 2 shows a diagram and table outlining the BS-Seq and oxBS-Seq techniques. BS-Seq consists of bisulfite treatment of the input DNA and then amplification followed by sequencing. oxBS-Seq consists of metal (VI) oxo complex treatment of the input DNA, followed by bisulfite treatment and amplification then sequencing. By comparing the input, BS-Seq and oxBS-Seq outputs C, 5mC and 5hmC can be discriminated, mapped and quantified.

Table 1 shows sequencing outcomes for cytosine and modified cytosines subjected to various treatments.

Table 2 shows the structures of cytosine (1a), 5-methylcytosine (5mC; 1b), 5-hydroxymethylcytosine (5hmC; 1c) and 5-formylcytosine (5fC; 1d)

EXPERIMENTS

Materials
Preparation of Alkaline Aqueous $M(VI)O_4^{2-}$ Solutions

Solid stocks of potassium ferrate, potassium manganate, potassium ruthenate, potassium osmate dehydrate, rhenium oxide and potassium molybdate were obtained from commercial sources at the highest purity possible (Alfa Aesar).
Preparation of Ruthenate(VI)
1. Reduction of Potassium Perruthenate(VII) by Hydroxide.

A 150 mM solution of potassium perruthenate was prepared by dissolving the appropriate mass of $KRuO_4$ in 500 mM NaOH. Complete dissolution of the solid was achieved by vortexing, affording a solution golden yellow/brown in colour. This solution was incubated at 25° C. for 48 hours. After the incubation period, the solution turned a deep blood red and was accompanied by the evolution of a gas ($O_2$).

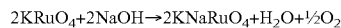

Figure 1:
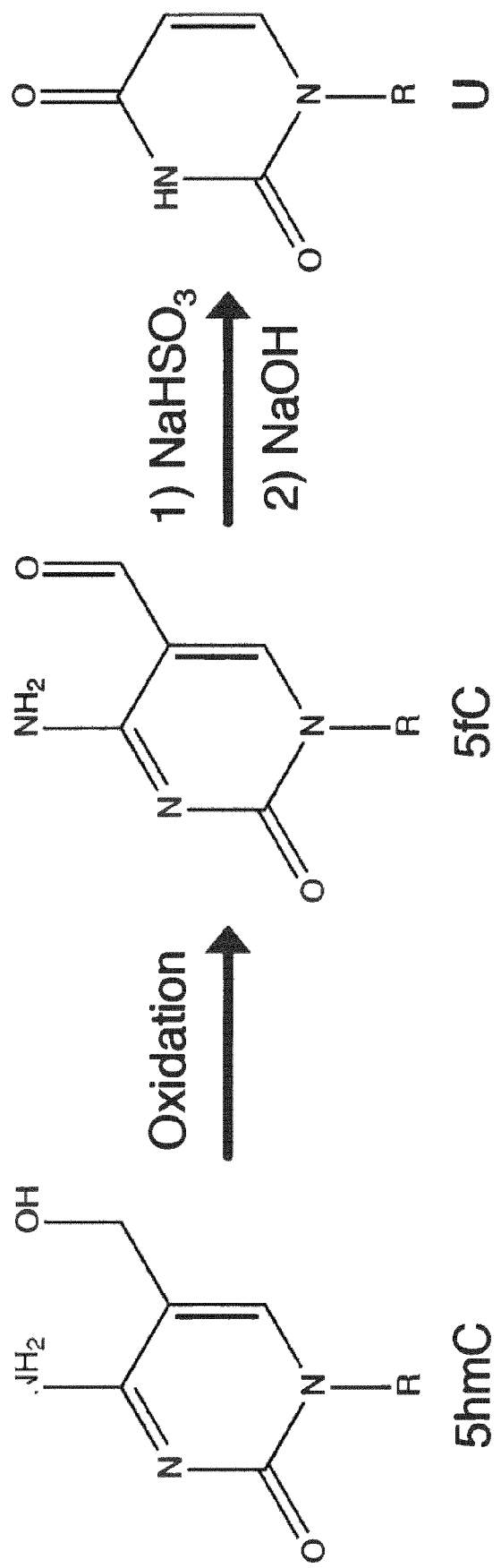
Figure 2:
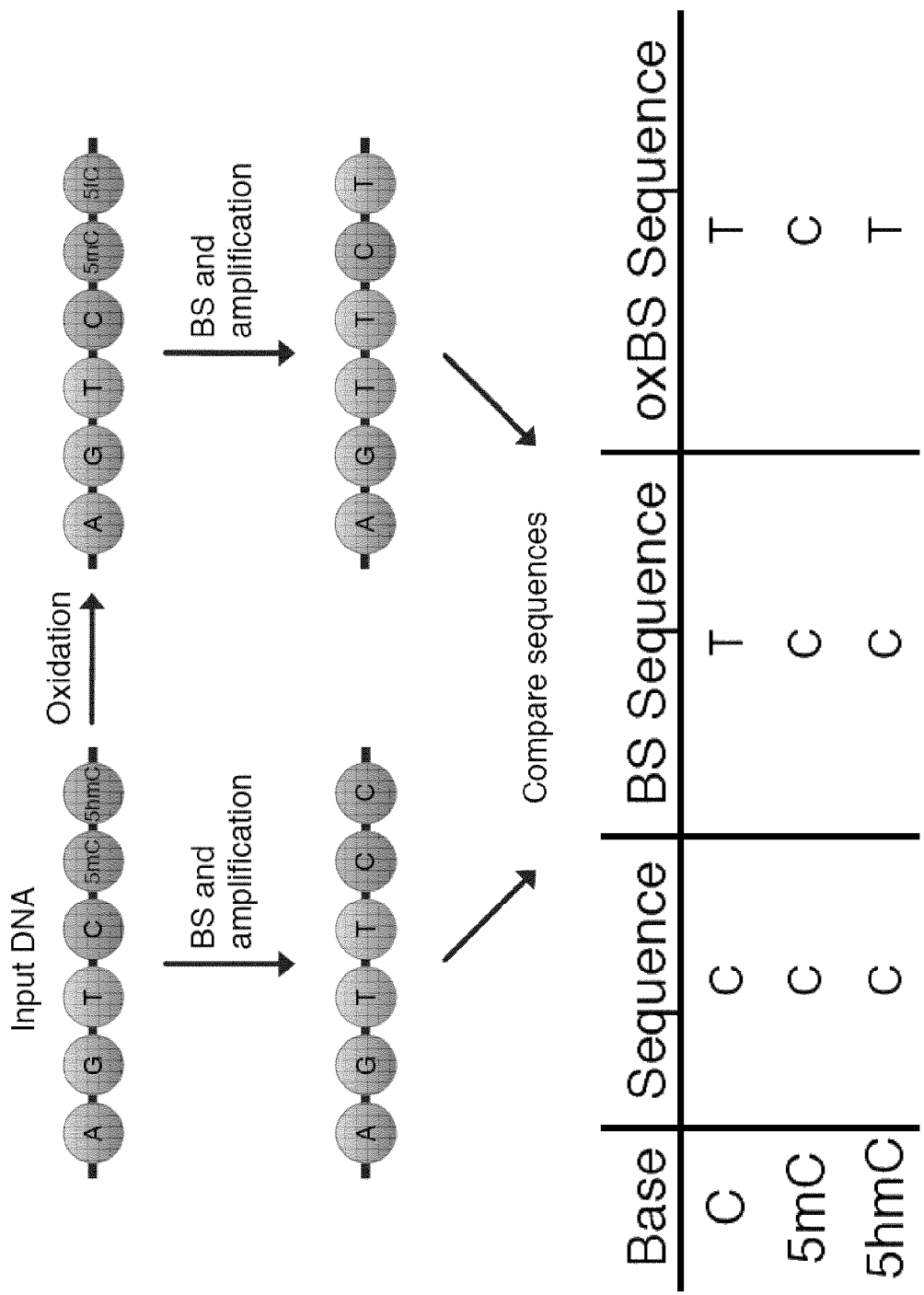
Figure 3:
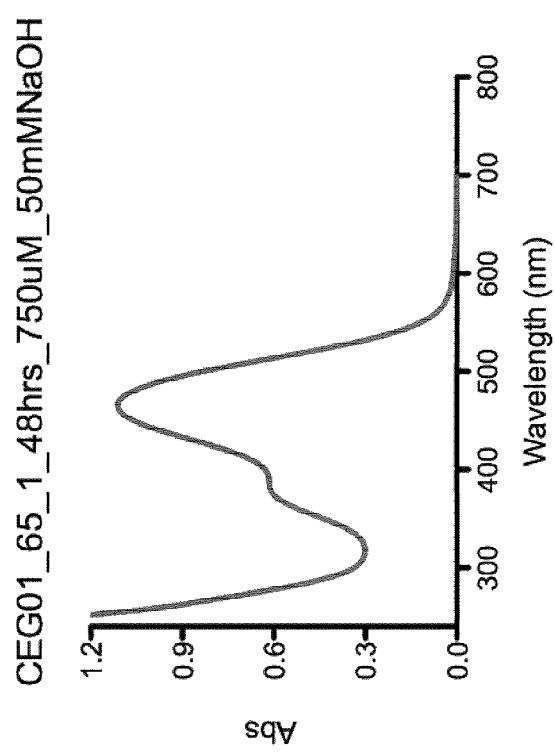
FIG. 3 shows the UV/visible spectrum of 750 µM $RuO_4^{2-}$ in 50 mM NaOH.
Figure 4:
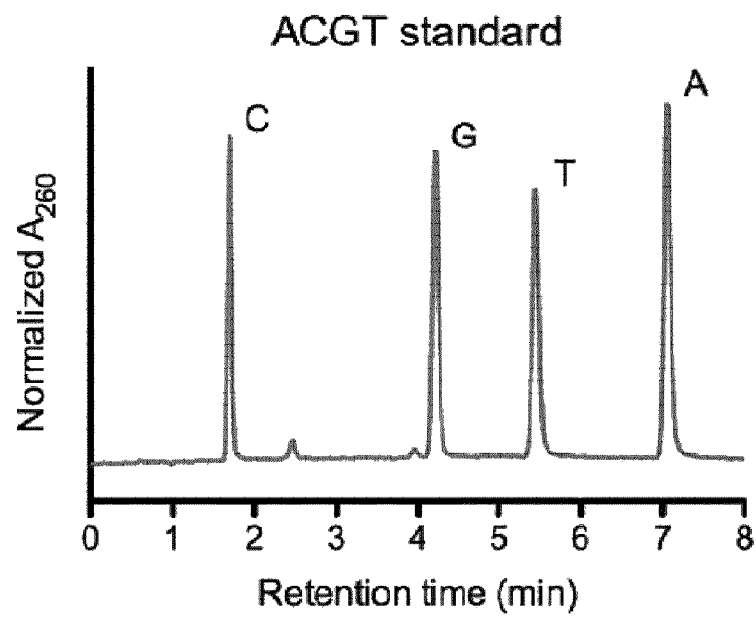
FIG. 4 shows an HPLC trace of unoxidised nucleotides A, C, T and G.
Figure 5:
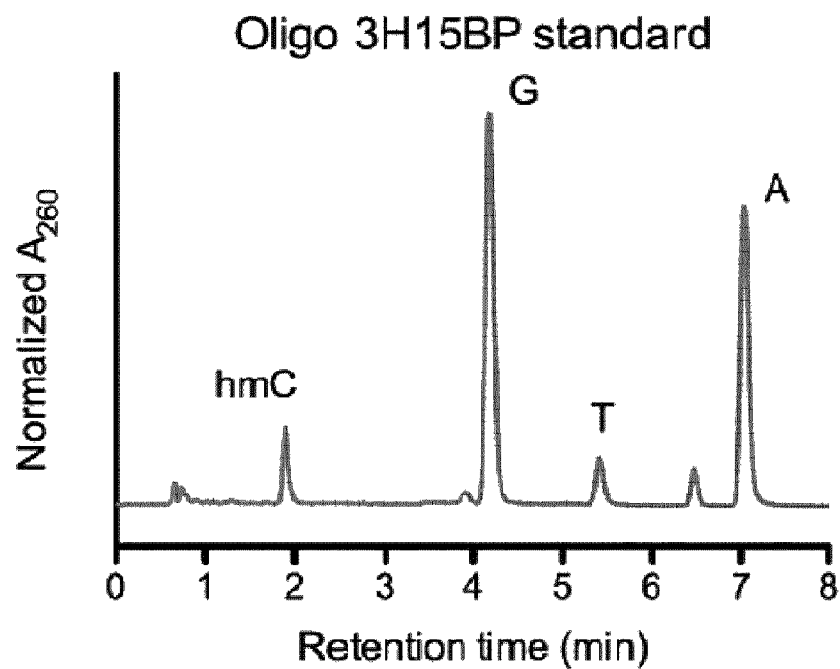
FIG. 5 shows an HPLC trace of the unoxidised 3H15BP oligonucleotide which contains three 5hmC residues.

Complete conversion within the 48 hour incubation period was demonstrated by UV/vis spectrophotometry (FIG. 2).
2. Direct Dissolution of Sodium Ruthenate (VI) in Sodium Hydroxide.

Direct preparation of a 150 mM solution of sodium ruthenate(VI) in 500 mM sodium hydroxide was tested. The solid $Na_2RuO_4$ is particularly insoluble and after more than a week at 25° C., complete dissolution of the solid under these conditions was not achieved. A UV/visible spectrum of the sparingly soluble fraction that did dissolve was taken and shown to be identical to the spectrum of ruthenate in the literature and to that prepared via Method 1.
Preparation of Manganate (VI)

Decomposition of potassium permanaganate(VII) by heating Heating causes solid potassium permanagante to decompose to manganate with the concomitant release of oxygen, according to the equation below:

Dissolving solid $K_2MnO_4$ in 500 mM NaOH affords a green solution of $K_2MnO_4$.
UV/Vis Spectrophotometry Certain alkaline aqueous solutions of $M(VI)O_4^{2-}$ are highly coloured and hence are easily characterised by UV/vis spectroscopy.

Spectra of alkaline aqueous $M(VI)O_4^{2-}$ solutions were taken using a Cary Varian 100 UV/vis spectrophotometer, in a 1 cm path length quartz glass cuvette (1 mL volume). Typical solution composition was 750 µM $M(VI)O_4^{2-}$ in 50 mM NaOH. Spectra were collected over the range 240-800 nm at a resolution of 1 nm at 25° C. All spectra were subjected to a baseline correction comprising subtraction of a 50 mM NaOH solution blank from each $M(VI)O_4^{2-}$ spectrum.
HPLC Oligonucleotide Oxidation and Digest Assay A qualitative HPLC assay used to visualize the oxidative conversion of 5-hmC to 5-fC. Digestion cuts the oligonucleotide into nucleoside monomers that can be uniquely resolved by chromatography, each monomer (A, C, G, T, U, 5-fC, 5-caC and 5-hmC) having a characteristic and predictable retention time defined analytical conditions. This allows the qualitative evaluation of (e.g.) the oxidation of 5-hmC to 5-fC.

A 100 uM stock of the 15 mer oligonucleotide 3H15BP (5' GAGACGACGTACAGG-3', where C is 5hmC) was employed. 3H15BP contains three 5-hmC residues.
Oligonucleotide Oxidation Solutions of 8 µM 3H15BP in 50 mM NaOH were prepared (20.75 uL MilliQ water, 1.25 µL 1 M NaOH, 2 µL 100 µM 3H15BP) and mixed by briefly vortexing. These were then incubated at 37° C. for 5 minutes to denature any secondary structure and then snap cooled on iced water (0° C.) for 5 minutes. Oxidation was initiated by the addition to the equilibrated alkaline oligo solution of 2 µL of a 15 mM $M(VI)O_4^{2-}$ solution in 50 mM NaOH. Once added, the oxidation solution was mixed by briefly vortexing and then returned to the iced water for 60 minutes. The oxidation reaction was mixed by vortexing twice during the 60 minute oxidation after 20 and 40 minutes. After each mix, the reaction was returned to the iced water.
Oxidized Oligonucleotide Purification After completion of the 60 minute oxidation, the oxidised oligonucleotide solutions were purified using a pre-washed (4×600 uL MilliQ) Roche oligo spin column. Eluate from the column was used as the input for the digestion reaction.

Oligonucleotide Digestion

Oxidized oligonucleotides were digested using the digestion cocktail (22 μL oxidized oligo+23 μL MilliQ+5 uL 10× digestion buffer+0.2 μL digestion cocktail) for 12 hours at 37° C.

Digestion cocktail was made up of 156U benzonase+100U alkaline phosphatase+0.15 mU phosphodiesterase I.

After digestion, samples were passed through a 3 kDa Amicon filter by centrifugation to remove enzymes from the sample.

HPLC Assay

Digested, oxidised oligonucleotides were analysed by HPLC using an Agilent 1100 HPLC with a flow of 1 mL/min over an Eclipse XDB-C18 3.5 μm, 3.0×150 mm column. The column temperature was maintained at 45 degrees. Eluting buffers were buffer A (500 mM Ammonium Acetate (Fisher) pH 5), Buffer B (Acetonitrile) and Buffer C ($H_2O$). Buffer A was held at 1% throughout the whole run and the gradient for the remaining buffers was 0 min—0.5% B, 2 min—1% B, 8 min—4% B, 10 min—95% B.

The retention times of 2'-deoxynucleosides are as follows: 2'-deoxy-5-carboxycytidine (1.0 min), 2'-deoxycytidine (1.8 min), 2'-deoxy-5-hydroxymethylcytidine (2.1 min), 2'-deoxyuridine (2.7 min), 2'-deoxy-5-methylcytidine (4.0 min), 2'-deoxyguanosine (4.5 min), 2'-deoxy-5-formylcytidine (5.4 min), 2'-deoxythymidine (5.7 min), 2'-deoxyadenosine (7.4 min).

Figure 6:
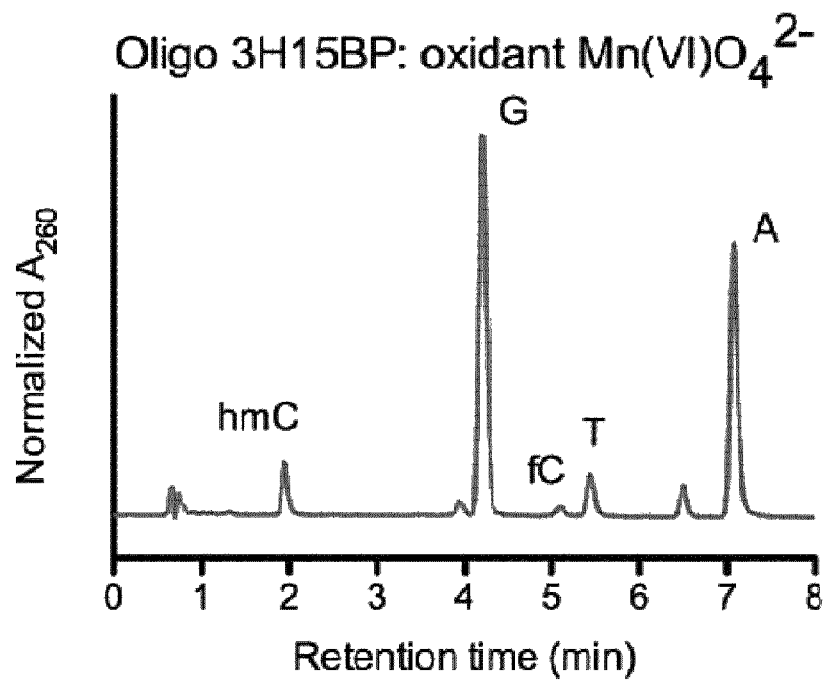
FIG. 6 shows an HPLC trace of the 3H15BP oligonucleotide following oxidation with $Mn(VI)O_4^{2-}$.
Figure 7:
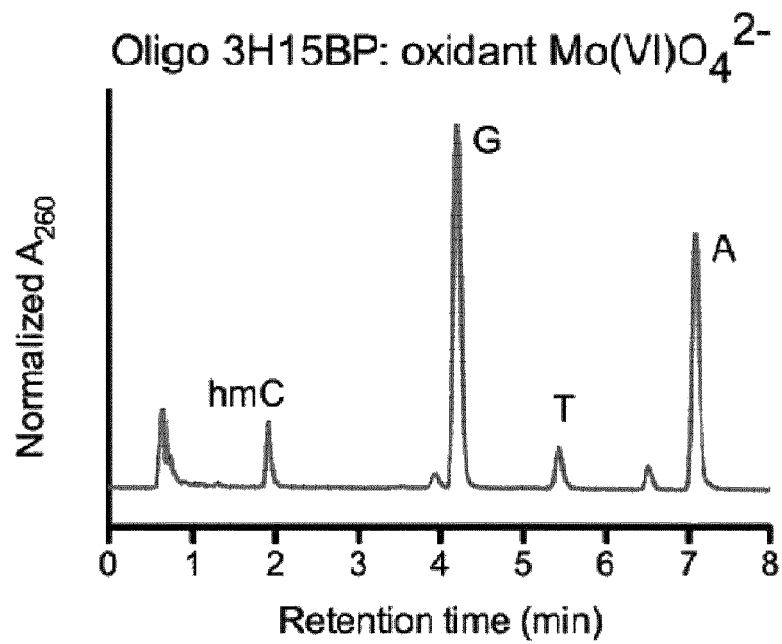
FIG. 7 shows an HPLC trace of the 3H15BP oligonucleotide following oxidation with $Mo(VI)O_4^{2-}$.
Figure 8:
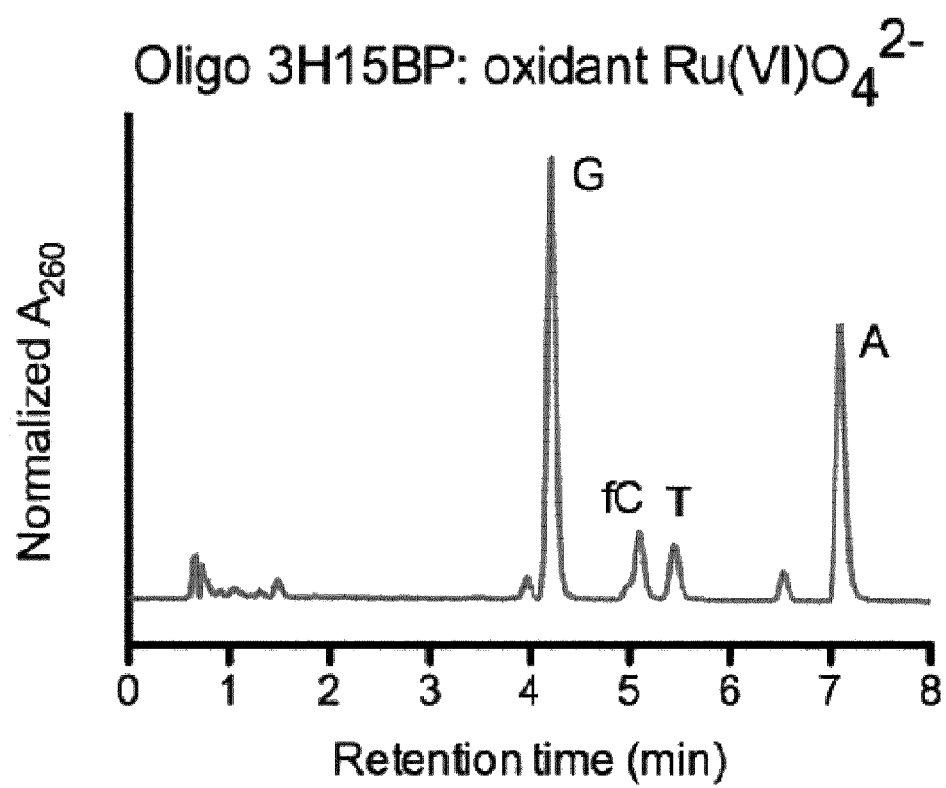
FIG. 8 shows an HPLC trace of the 3H15BP oligonucleotide following oxidation with $Ru(VI)O_4^{2-}$.

The results of HPLC analysis following traces from oligonucleotide oxidation with manganate, molybdate and ruthenate are shown in FIGS. 6-8. Ruthenate was found to efficiently oxidise 5hmC to 5fC. Manganate was found to oxidise 5hmC to a lesser extent that ruthenate. No oxidation of 5hmC was observed with molybdate under these conditions.

REFERENCES

1. A. M. Deaton et al Genes Dev. 25, 1010 (May 15, 2011).
2. M. Tahiliani et al. Science 324, 930 (May 15, 2009).
3. S. Ito et al. Nature 466, 1129 (Aug. 26, 2010).
4. A. Szwagierczak et al Nucleic Acids Res, (Aug. 4, 2010).
5. K. P. Koh et al. Cell Stem Cell 8, 200 (Feb. 4, 2011).
6. G. Ficz et al., Nature 473, 398 (May 19, 2011).
7. K. Williams et al. Nature 473, 343 (May 19, 2011).
8. W. A. Pastor et al. Nature 473, 394 (May 19, 2011).
9. Y. Xu et al. Mol. Cell 42, 451 (May 20, 2011).
10. M. R. Branco et al Nat. Rev. Genet. 13, 7 (January 2012).
11. S. Kriaucionis et al Science 324, 929 (May 15, 2009).
12. M. Munzel at al. Angew. Chem. Int. Ed. 49, 5375 (July 2010).
13. H. Wu et al. Genes Dev. 25, 679 (Apr. 1, 2011).
14. S. G. Jin et al Nuc. Acids. Res. 39, 5015 (July 2011).
15. C. X. Song et al. Nat. Biotechnol. 29, 68 (January 2011).
16. M. Frommer et al. PNAS. U.S.A. 89, 1827 (March 1992).
17. Y. Huang et al. PLoS One 5, e8888 (2010).
18. C. Nestor et al Biotechniques 48, 317 (April 2010).
19. C. X. Song et al. Nat. Methods, (Nov. 20, 2011).
20. J. Eid et al. Science 323, 133 (Jan. 2, 2009).
21. E. V. Wallace et al. Chem. Comm. 46, 8195 (Nov. 21, 2010).
22. M. Wanunu et al. J. Am. Chem. Soc., (Dec. 14, 2010).
23. Booth et al (2012) Science 336 934
24. Wu H et al. Science. 2010; 329(5990):444-448
25. van den Boom D DNA Methylation: Methods and Protocols. Vol. 507, 2nd ed (2008):207-227.
26. Howell W M. et al (January 1999). Nat. Biotechnol. 17(1): 87-8
27. Abravaya K et al (2003). Clin. Chem. Lab. Med. 41 (4):468-74.
28. Harbron S et al (2004). Molecular analysis and genome discovery. London: John Wiley ISBN 0-471-49919-6.
29. Newton, C. R. et al Nucl. Acids Res. 17:2503-2516, 1989
30. Wu, D. Y. et al. PNAS USA, 86:2757-2760, 1989
31. Okayama, H. et al J. Lab. Clin. Med. 114:105-113, 1989
32. Olivier M (June 2005) Mutat. Res. 573 (1-2): 103-10.
33. Gunderson K L, (2006 Meth. Enzymol. Methods in Enzymology 410: 359-76.
34. Syvänen A C (December 2001) Nat. Rev. Genet. 2 (12): 930-42.
35. Molecular Diagnostics $2^{nd}$ Edition (2010) edited by George Patrinos, Wilhelm Ansorge Elseveir ISBN 978-0-12-374537-8
36. McGuigan F E (2002) Psychiatr. Genet. 12 (3): 133-6
37. Jarvius et al (2003) Methods in Molecular Biology 212 (2003) 215-228
38. Sanger, F. et al PNAS USA, 1977, 74, 5463
39. Bentley et al Nature, 456, 53-59 (2008)
40. K J McKernan et al Genome Res. (2009) 19: 1527-1541
41. M Ronaghi et al Science (1998) 281 5375 363-365
42. Bid et al Science (2009) 323 5910 133-138
43. Korlach et al Methods in Enzymology 472 (2010) 431-455)
44. Rothberg et al (2011) Nature 475 348-352
45. Li et al Nucleic Acids (2011) Article ID 870726
46. Pfaffeneder, T. et al (2011) Angewandte. 50. 1-6
47. Maeda et al Hum Immunol. (1990) 27(2):111-21.
48. Wang et al (2008) Electrophoresis April; 29(7):1490-501
49. Wolff et al (2008). BioTechniques 44 (2): 193-4, 196, 199
50. Zhang et al (2005). Nucleic Acids Res. 33: W489-92.
51. Hung et al (2008) BMC Biotechnology, 8:62
52. Lister, R. et al (2008) Cell. 133. 523-536
53. Wang et al (1980) Nucleic Acids Research. 8 (20), 4777-4790
54. Hayatsu et al (2004) Nucleic Acids Symposium Series No. 48 (1), 261-262
55. Lister et al (2009) Nature. 462. 315-22

TABLE 1

| Base | Regular Sequencing | Bisulfite Sequencing | Oxidation then Bisulfite Sequencing |
|---|---|---|---|
| C | C | U | U |
| 5 mC | C | C | C |
| 5 hmC | C | C | U |

TABLE 2

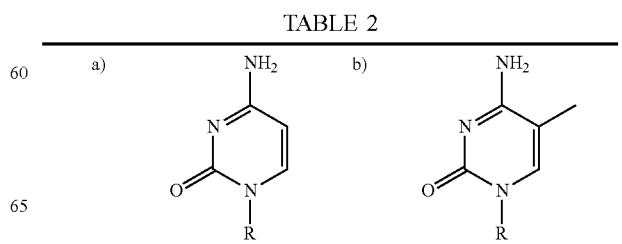

TABLE 2-continued

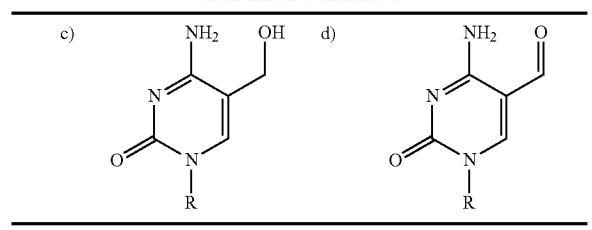

```
                        SEQUENCE LISTING

<160> NUMBER OF SEQ ID NOS: 1

<210> SEQ ID NO 1
<211> LENGTH: 15
<212> TYPE: DNA
<213> ORGANISM: Artificial sequence
<220> FEATURE:
<223> OTHER INFORMATION: Synthetic sequence: 15mer oligonucleotide
      3H15BP of PCT/EP2013/074995
<220> FEATURE:
<221> NAME/KEY: misc_feature
<222> LOCATION: (5, 8, 12)
<223> OTHER INFORMATION: n is 5hmC

<400> SEQUENCE: 1
gagangangt anagg                                                       15
``` sequence and sequencing the second portion of the population produces a second nucleotide sequence.

12. The method of claim 11, wherein (i) identification of a uracil at a position in the first nucleotide sequence and a cytosine at a same position in the second nucleotide sequence is indicative that the modified cytosine residue is 5hmC; (ii) identification of cytosine at a position in the first nucleotide sequence or in both the first nucleotide sequence and the second nucleotide sequence is indicative that the modified cytosine residue is 5-methylcytosine (5mC); or (iii) identification of a uracil at a position in both the first nucleotide sequence and the second nucleotide sequence is indicative that the modified cytosine residue is a cytosine, a 5fC or a 5-carboxylcytosine (5caC).

The invention claimed is:

1. A method comprising:
   providing a population of polynucleotides, wherein the population comprises a nucleotide sequence containing a modified cytosine residue; and
   treating at least a first portion of the population with a metal (VI) oxo complex, wherein the metal (VI) oxo complex converts 5-hydroxymethylcytosine (5hmC) residues in the first portion to 5-formylcytosine (5fC) residues, wherein the metal (VI) oxo complex comprises a manganate or a ruthenate.

2. The method of claim 1, wherein the metal (VI) oxo complex comprises the ruthenate.

3. The method of claim 2, wherein the ruthenate comprises $K_2RuO_4$.

4. The method of claim 1, wherein the metal (VI) oxo complex comprises the manganate.

5. The method of claim 4, wherein the manganate comprises $K_2MnO_4$.

6. The method of claim 1, further comprising treating the first portion and a second portion of the population with bisulfite.

7. The method of claim 6, further comprising subjecting the first portion and the second portion of the population to one or more amplification reactions after treating with bisulfite.

8. The method of claim 6, further comprising sequencing the first portion and the second portion of the population after bisulfite treatment.

9. The method of claim 8, wherein the sequencing comprises high throughput sequencing.

10. The method of claim 8, further comprising identifying the modified cytosine residue in the nucleotide sequence.

11. The method of claim 8, wherein sequencing the first portion of the population produces a first nucleotide sequence and sequencing the second portion of the population produces a second nucleotide sequence.

13. The method of claim 8, further comprising:
   contacting the first portion and second portion of the population with a detection oligonucleotide, wherein the detection oligonucleotide specifically hybridizes to a cytosine or a uracil at a position corresponding to the modified cytosine residue; and
   identifying a presence or absence of the modified cytosine residue in the nucleotide sequence based at least in part on hybridization of the detection oligonucleotide.

14. The method of claim 8, further comprising:
   contacting the first portion and the second portion of the population with a specific binding member, wherein the specific binding member specifically binds to polynucleotides comprising a cytosine or a uracil at a position corresponding to the modified cytosine residue in the nucleotide sequence; and
   identifying a presence or absence of the modified cytosine residue in the nucleotide sequence based at least in part on a binding of the specific binding member.

15. The method of claim 8, further comprising:
   subjecting the first portion and the second portion of the population to one or more amplification reactions, wherein the one or more amplification reactions amplify polynucleotides comprising a cytosine, a uracil, or a thymine at a position corresponding to the modified cytosine residue in the nucleotide sequence; and
   identifying a presence or absence of the modified cytosine residue in the nucleotide sequence based at least in part on an amplification product.

16. The method of claim 8, further comprising:
   hybridizing polynucleotides of the first portion and the second portion of the population with an oligonucleotide, wherein the oligonucleotide is complementary to a region that is 3' of the modified cytosine residue in the nucleotide sequence.

* * * * *